United States Patent [19]
Fields

[11] Patent Number: 5,840,573
[45] Date of Patent: Nov. 24, 1998

[54] MOLECULAR ANALYZER AND METHOD OF USE

[76] Inventor: Robert E. Fields, 1618 Sand Hill Rd., Palo Alto, Calif. 94304

[21] Appl. No.: 687,589
[22] PCT Filed: Feb. 1, 1995
[86] PCT No.: PCT/US95/01591
  § 371 Date: Oct. 3, 1996
  § 102(e) Date: Oct. 3, 1996
[87] PCT Pub. No.: WO95/21382
  PCT Pub. Date: Aug. 10, 1995

[30] Foreign Application Priority Data

Feb. 1, 1994 [GB] United Kingdom .................. 9401849
Feb. 8, 1994 [GB] United Kingdom .................. 9402357
Mar. 11, 1994 [GB] United Kingdom .................. 9404758
Mar. 21, 1994 [GB] United Kingdom .................. 9405565
Jul. 6, 1994 [GB] United Kingdom .................. 9413641
Oct. 24, 1994 [GB] United Kingdom .................. 9421378

[51] Int. Cl.[6] .............................. C12M 1/00; C12M 3/02; B01L 3/00; G05D 23/00
[52] U.S. Cl. .................. 435/287.2; 435/91.2; 435/286.6; 435/286.7; 422/102; 422/105; 422/109
[58] Field of Search .............................. 435/6, 91.1, 91.2, 435/287.2, 286.6, 286.7; 261/42, 158, 159; 422/3, 105, 109, 99, 106, 101, 102, 103, 104

[56] References Cited

U.S. PATENT DOCUMENTS

3,036,894 5/1962 Forestiere .................................. 23/230
3,616,264 10/1971 Ray et al. ............................... 195/127

(List continued on next page.)

FOREIGN PATENT DOCUMENTS

281 201 9/1988 European Pat. Off. .
320 240 6/1989 European Pat. Off. .
2 612 295 9/1988 France .
WO 86/00704 1/1986 WIPO .
WO 92/20778 11/1992 WIPO .

OTHER PUBLICATIONS

Ericomp, "Peltier Power" advertisement (1994).
Idaho Technology, "The 1605 Air Thermo–Cycler: Light Speed Thermo–Cycling" brochure *PCR Protocols: A Guide to Methods and Applications,* pp. 142–145, 337–347 (Michael A. Innis et al., eds., 1990).
Perkin Elmer, "A Decade of PCR: in Celebration of Ten Years of Amplification" advertisement, *PCR: Methods and Applications,* 4, 1 (1994).
Perkin Elmer, "1992•1993 Biotechnology Catalog," pp. 40–43, 45 (1992/1993).
Roche, "Super Power of PCR to Clinical Diagnostic Testing" brochure Stratagene, Robocycler™ 40 Temperature Cycler Instruction Manual, pp. 3, 6 (1993).
Wittwer, C.T. et al., "Automated Polymerase Chain Reaction in Capillary Tubes with Hot Air," *Nucleic Acids Research,* 17, 11, pp. 4353–4357 (1989).

(List continued on next page.)

*Primary Examiner*—Bradley L. Sisson
*Attorney, Agent, or Firm*—Fish & Neave; James F. Haley, Jr.; Jennifer T. Weissman

[57] ABSTRACT

A molecular analyzer and method of use for sensitive, rapid and accurate detection of specific, or target, molecules or specific parts of molecules in a liquid sample to be detected without the use of radioisotopes. Apparatus for sealingly holding any number of sample tubes (23) containing a test sample and having pre-incorporated, internally contained detection reagents for removing unbound molecules from the sample tubes, as well as means for rapidly changing the temperature of the test sample and means for quantitating the target molecules without allowing molecules in the sample tube to contact the environment is provided. Alternatively, the apparatus may be adapted to receive detection reagents that are not preincorporated without exposing them or the test sample to the atmosphere.

29 Claims, 17 Drawing Sheets

5,840,573
Page 2

U.S. PATENT DOCUMENTS

| | | | |
|---|---|---|---|
| 3,647,386 | 3/1972 | Gilford | 23/230 |
| 3,690,836 | 9/1972 | Buissiere et al. | 23/253 |
| 3,691,017 | 9/1972 | Brown et al. | 195/103.5 |
| 3,713,779 | 1/1973 | Sirago et al. | 23/259 |
| 3,726,645 | 4/1973 | Kaczmarek | 23/253 |
| 3,740,196 | 6/1973 | Stroterhoff | 23/253 |
| 3,799,742 | 3/1974 | Coleman | 23/253 |
| 3,994,594 | 11/1976 | Sandrock et al. | 356/246 |
| 3,998,719 | 12/1976 | Deml et al. | 204/299 |
| 4,007,010 | 2/1977 | Woodbridge, III | 23/253 R |
| 4,038,055 | 7/1977 | Varano et al. | 55/197 |
| 4,065,263 | 12/1977 | Woodbridge, III | 23/253 TP |
| 4,119,407 | 10/1978 | Goldstein et al. | 422/58 |
| 4,286,456 | 9/1981 | Keim et al. | 260/455 R |
| 4,420,679 | 12/1983 | Howe | 219/400 |
| 4,585,623 | 4/1986 | Chandler | 422/57 |
| 4,673,657 | 6/1987 | Christian | 436/501 |
| 4,683,195 | 7/1987 | Mullis et al. | 435/6 |
| 4,683,202 | 7/1987 | Mullis | 435/91 |
| 4,690,801 | 9/1987 | Anderson | 422/68 |
| 4,701,415 | 10/1987 | Dutton et al. | 435/289 |
| 4,747,919 | 5/1988 | Anderson | 204/182.8 |
| 4,756,884 | 7/1988 | Hillman et al. | 422/73 |
| 4,800,159 | 1/1989 | Mullis et al. | 435/172.3 |
| 4,806,313 | 2/1989 | Ebersole et al. | 422/61 |
| 4,810,653 | 3/1989 | Helfer et al. | 435/316 |
| 4,865,986 | 9/1989 | Coy et al. | 435/290 |
| 4,902,624 | 2/1990 | Columbus et al. | 435/316 |
| 4,965,188 | 10/1990 | Mullis et al. | 435/6 |
| 4,981,801 | 1/1991 | Suzuki et al. | 435/290 |
| 5,038,852 | 8/1991 | Johnson et al. | 165/12 |
| 5,082,780 | 1/1992 | Warren, III et al. | 435/191 |
| 5,116,576 | 5/1992 | Stanley | 422/55 |
| 5,154,888 | 10/1992 | Zander et al. | 422/50 |
| 5,176,203 | 1/1993 | Larzul | 165/61 |
| 5,187,084 | 2/1993 | Hallsby | 435/91 |
| 5,219,727 | 6/1993 | Wang et al. | 435/6 |
| 5,254,479 | 10/1993 | Chemelli | 436/180 |
| 5,282,543 | 2/1994 | Picozza et al. | 220/255 |
| 5,304,487 | 4/1994 | Wilding et al. | 435/291 |
| 5,333,675 | 8/1994 | Mullis et al. | 165/12 |
| 5,338,671 | 8/1994 | Scalice et al. | 435/91.2 |
| 5,455,175 | 10/1995 | Wittwer et al. | 435/286.1 |

OTHER PUBLICATIONS

Wittwer, C.T. et al., "Rapid Cycle Allele–Specific Amplification: Studies with the Cystic Fibrosis $\Delta F_{508}$ Locus," *Clinical Chemistry,* 39, 5, pp. 804–809 (1993).

Wittwer, C.T. and Garling, D.J., "Rapid Cycle DNA Amplification: Time and Temperature Optimization," *Bio Techniques,* 10, 1, pp. 76–83 (1991).

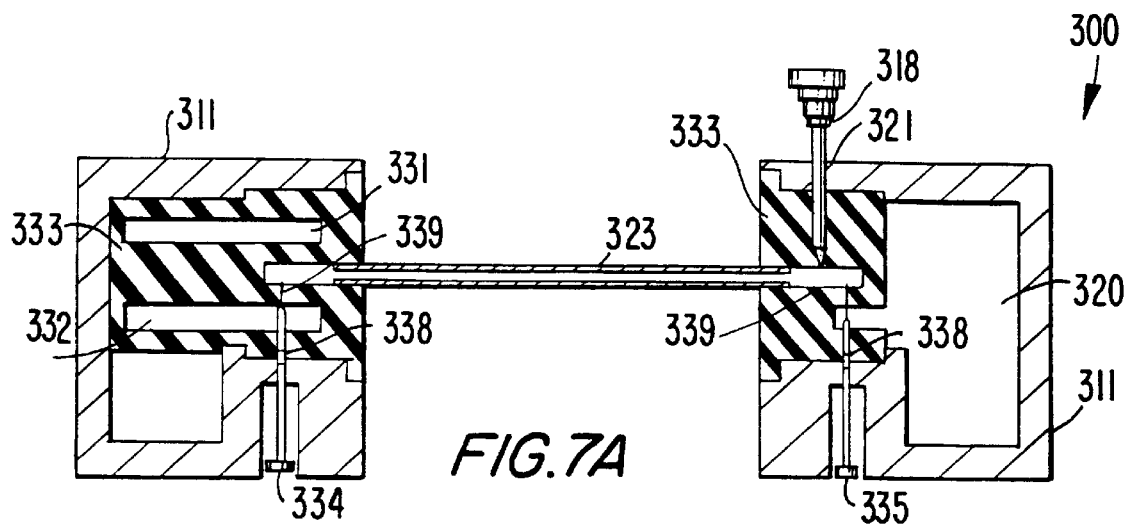
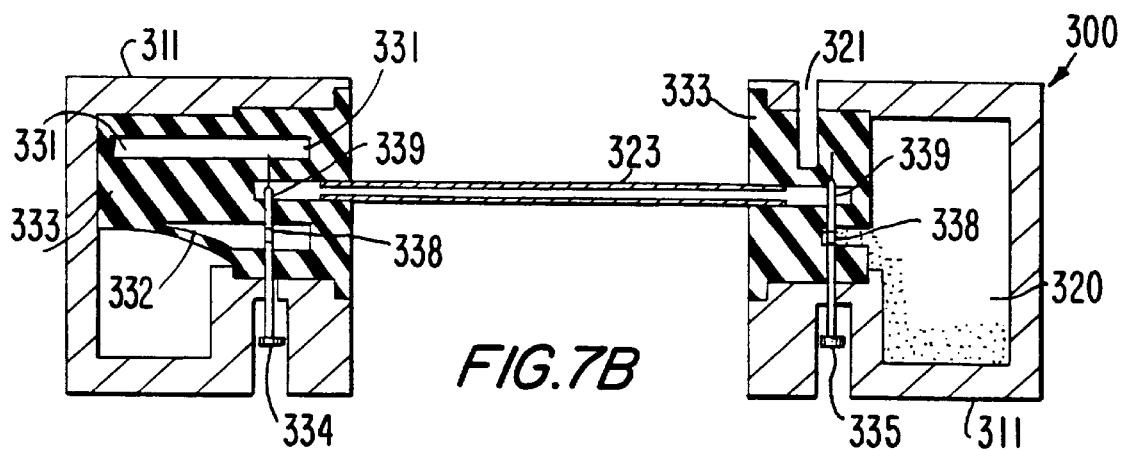
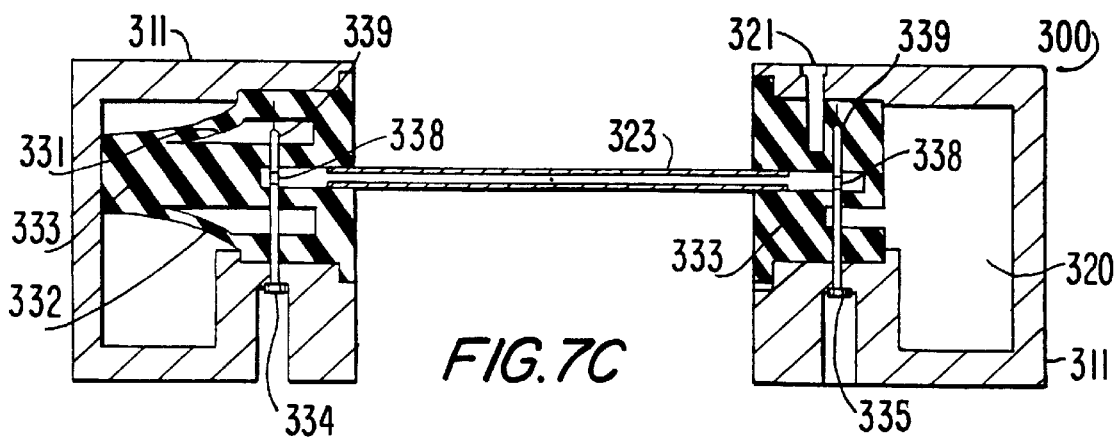

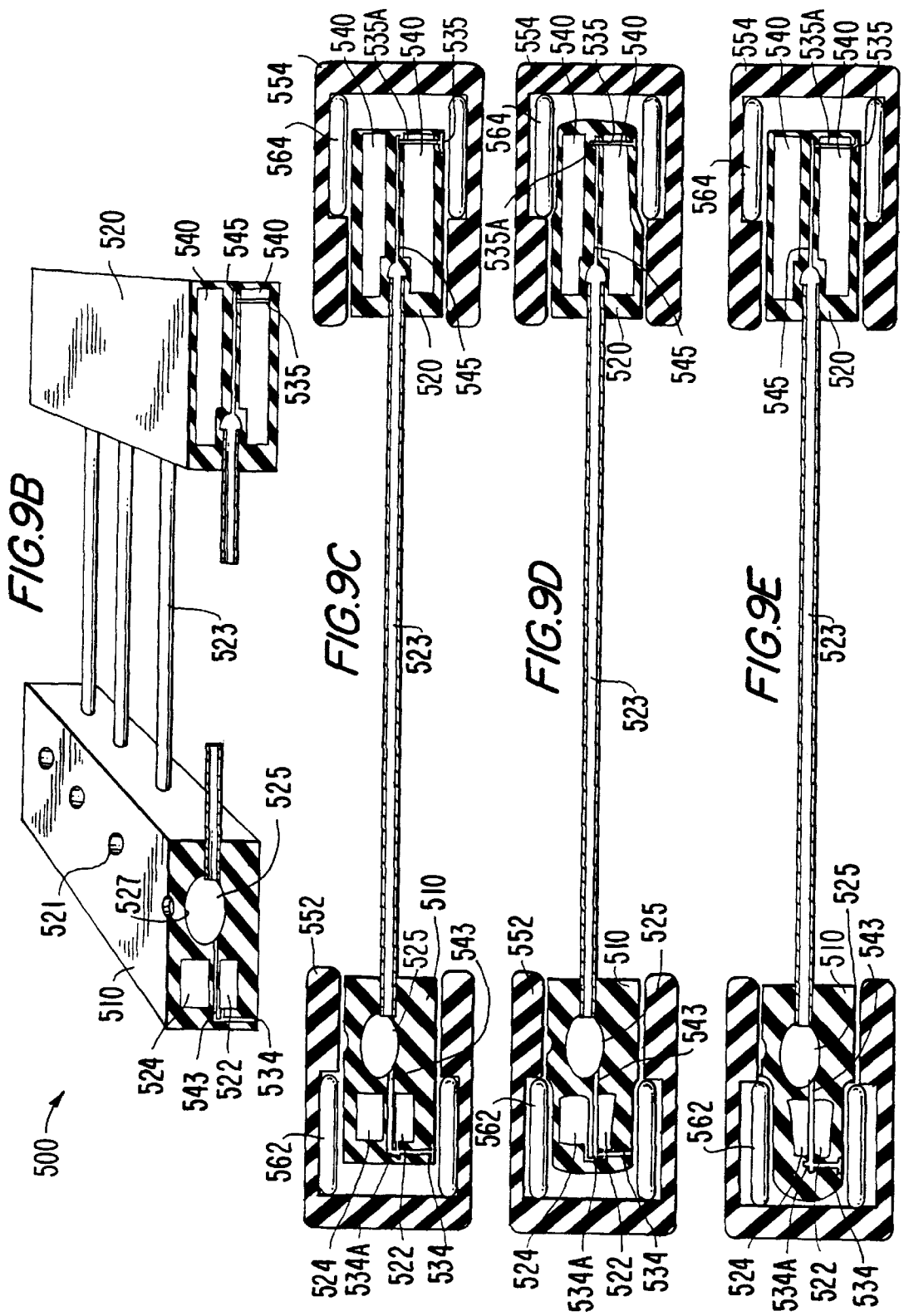

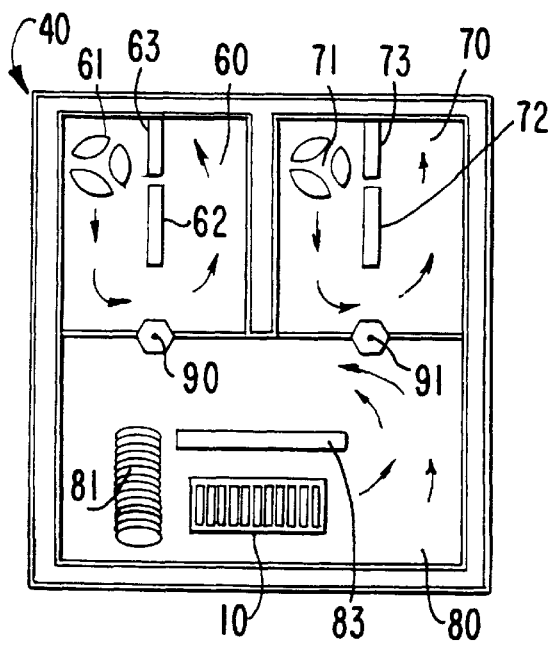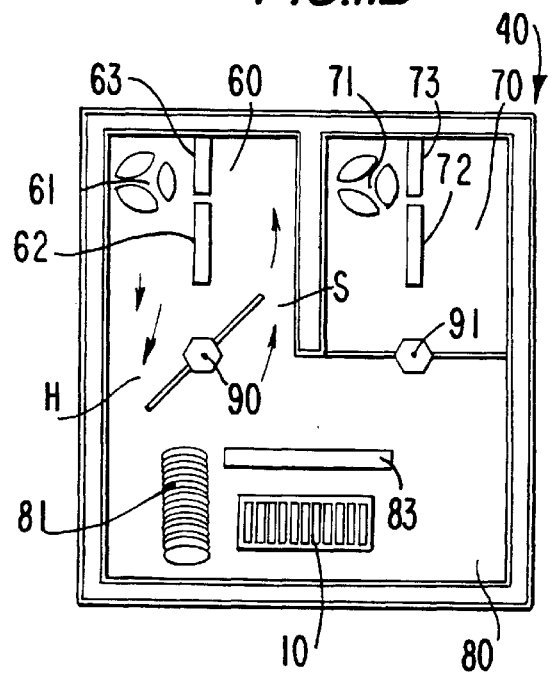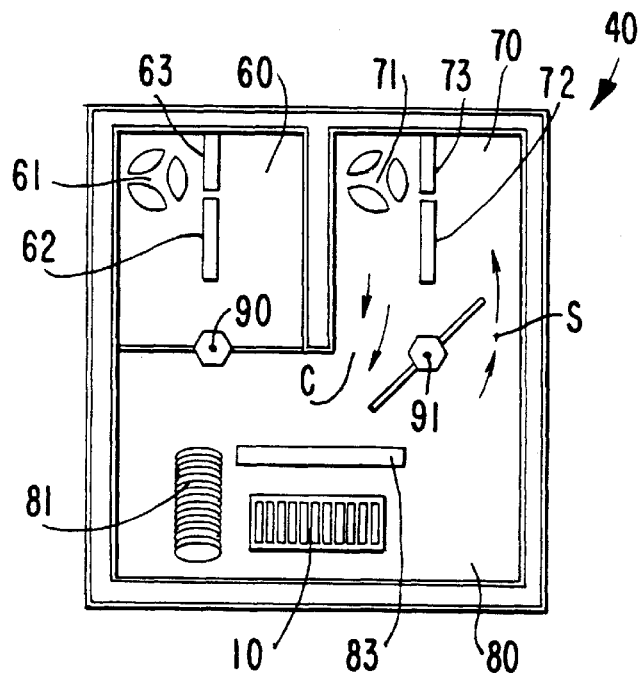

FIG.14A
FIG.14B
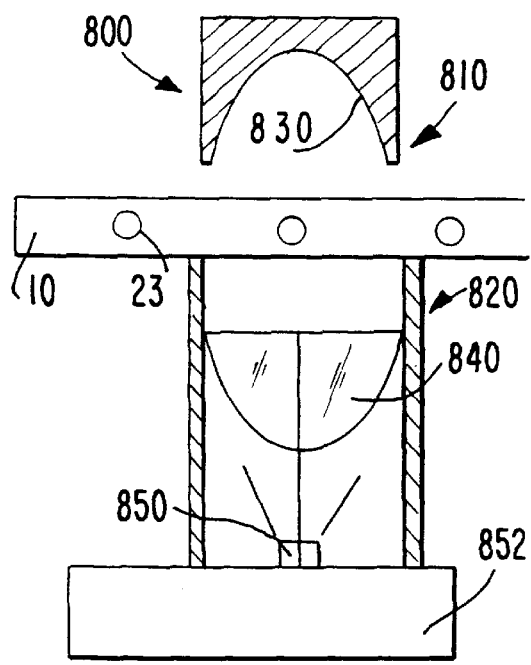
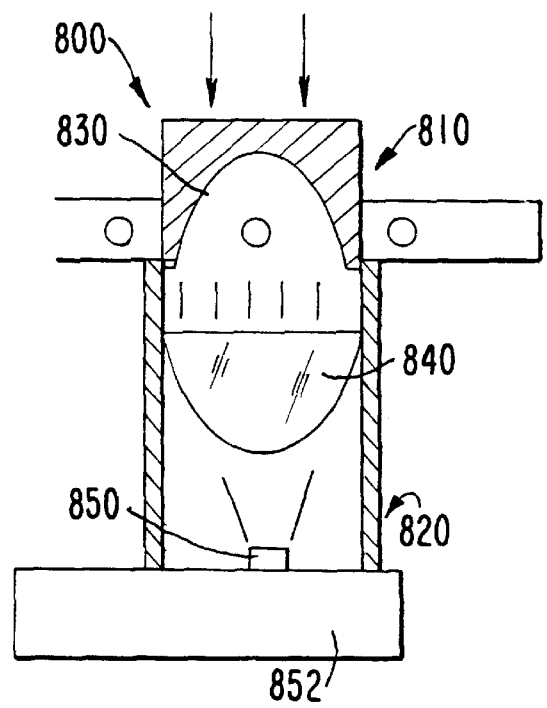

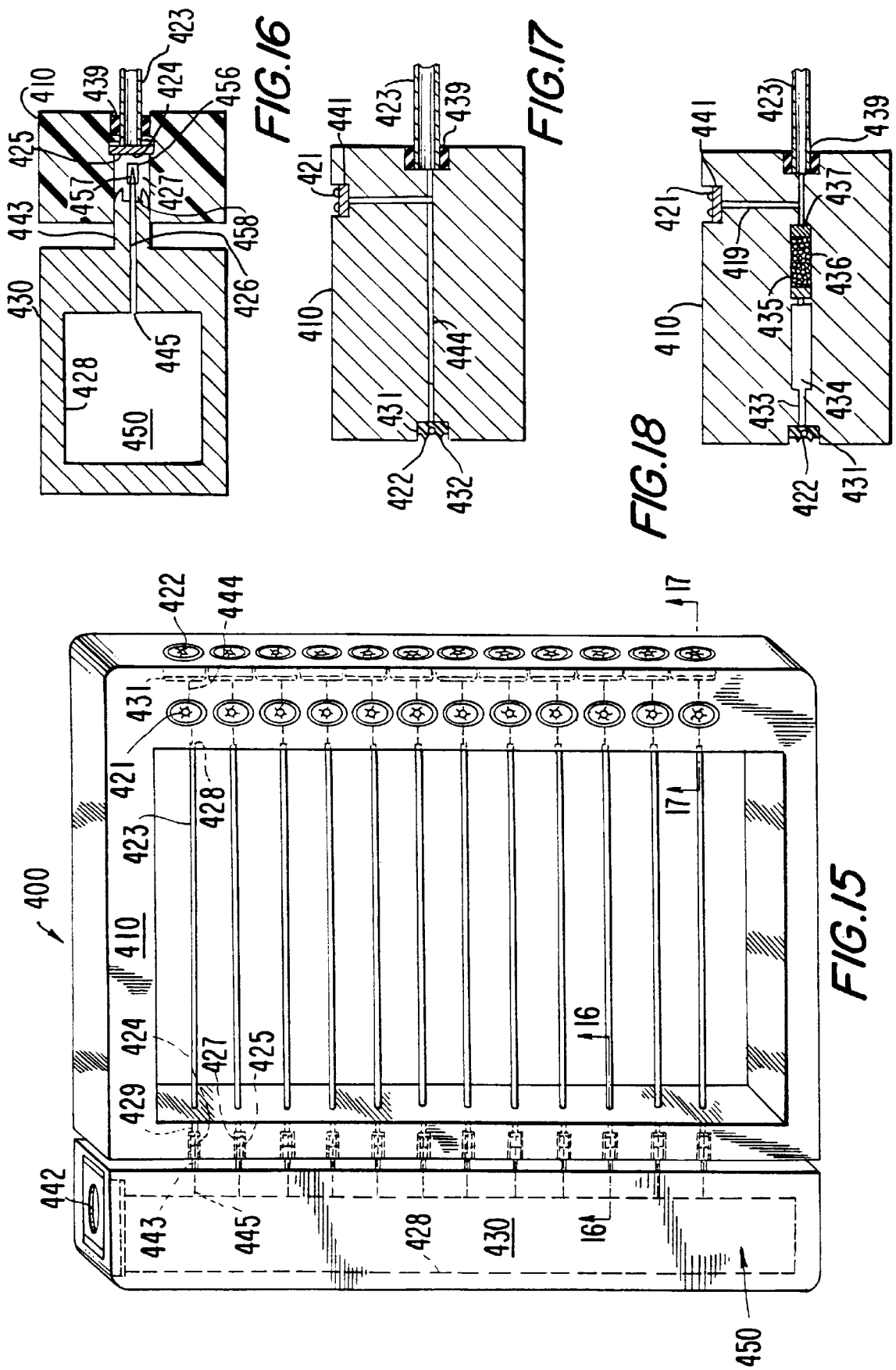

MOLECULAR ANALYZER AND METHOD OF USE

BACKGROUND OF THE INVENTION

The present invention relates to a molecular analyzer and method of use that enables specific molecules in a liquid sample, or specific parts of molecules in a liquid sample, to be rapidly and accurately detected. The molecules may be present as independent entities in solution or as part of molecular complexes associated by weak or by covalent bonds. In the case of biopolymers, the element detected may be restricted to a unique physical configuration such as an epitope on a protein or a particular sequence of nucleotide bases in a larger RNA or DNA molecule.

There is a widespread need by scientists and technical workers to have means for safely carrying out experiments that employ substances which may be radioactive, carcinogenic, corrosive, toxic or infectious. Diagnostic tests using blood or laboratory experiments employing biologically active compounds or radioisotopes carry a risk of contamination of the environment and harm to personnel, particularly if these tests or experiments involve manual manipulations of samples. Other risks of contamination arise when the products of a chemical or enzymatic reaction are themselves deleterious. An example of such is the polymerase chain reaction ("PCR"), which permits the amplification a specific nucleic acid sequence many million-fold. If traces of the amplified product from one experiment escape into the environment, they may contaminate a second PCR experiment, and serving as a template for amplification, falsely indicate the presence of the original nucleic acid sequence in the second sample. Contamination by even a single molecule of amplified product from one experiment is sufficient to generate a false-positive signal in another experiment. The present invention is described primarily in terms of embodiments adapted to carry out PCR, but those of skill in the art will recognize that the present invention is equally applicable to other chemical reactions or means of analyses.

Use of PCR for the detection of Human Immunodeficiency Virus-1 ("HIV"), the causative agent of Acquired Immune Deficiency Syndrome ("AIDS"), has provided a means for detecting small numbers of HIV nucleic acid molecules in blood. Similarly, accurate detection of minute amounts of other pathogens is possible using PCR. However, even though it is well-known that PCR tests provide for a direct detection of pathogens and are potentially more sensitive than other methods that are based on screening for surrogate markers, PCR is not in widespread clinical use at present. This is due to the higher cost of testing using PCR and the practical difficulties of preventing contamination of the testing facility. Thus, PCR has not been used by Blood Banks to protect the blood supply from HIV or other pathogens and has not been routinely used in the clinical diagnostic, biotechnological, pharmaceutical or food industries where its sensitivity would confer greater benefits than tests currently being used.

PCR is a process for amplifying and detecting any target nucleic acid sequence if it is present in a test sample. In general, it is carried out as follows. A test sample that may contain target double-stranded DNA is first heated to separate the two complementary strands that make up the DNA double helix. Each separated DNA strand becomes a template for making a mirror-image of copy itself. The DNA solution is then cooled in the presence of short complimentary DNA strands and DNA polymerase, an enzyme that extends the DNA strands until a new mirror-image copy is made of the original template, and two new double helix DNA molecules are generated.

If the solution is heated again to melting temperature, the strands of the two newly-formed DNA molecules separate to become four template strands. Further cycling of the reaction mixture exponentially increases the number of DNA molecules. After thermal cycling, the molecules of amplified DNA are detected by any of a number of laboratory methods known to those of skill in the art.

PCR as described by Mullis in U.S. Pat. No. 4,683,202 was performed manually. Improvements have since been made in the chemistry and apparatus for carrying out temperature cycling, but other areas have remained labor intensive, such as preparing samples, manually loading sample tubes and removing solutions from sample tubes after thermal cycling. Many techniques have been developed for detecting the amplified product. The most sensitive detection techniques, such as using liquid hybridization with a radioactive probe followed by gel electrophoresis and autoradiography, require the use of radioisotopes and are time-consuming and labor intensive. Other detection methods using immobilized hybridization probes in microtiter plates are more rapid but have a high cost and suffer from the problem of DNA contamination.

Contamination of test facilities is a critical problem that is exacerbated by the present methods of detection of amplified DNA. For example, when a sample tube is opened after thermal cycling, aerosols are released that contain molecules of the amplified DNA. Even with the use of contaminant hoods and strictly controlled working conditions, it has been almost impossible to prevent the contamination of a test facility with molecules of amplified DNA, known as "carryover DNA."

Temperature cycling as described by Mullis was performed manually using a temperature controlled water bath and a microfuge tube that contained a buffered solution of DNA template, a molar excess of two oligonucleotide primers, nucleotide triphosphates and DNA polymerase. Since that time a large literature has developed describing improvements in the chemistry, product detection and apparatus for carrying out temperature cycling. Programmable temperature cyclers using solid heating blocks, temperature controlled water and hot air have been described. State of the art thermal cyclers using metal heating blocks have thermal transition rates in the range of 1° Celsius per second and usually require 60 to 90 minutes to carry out 30 cycles of PCR amplification. Using standard detection methods, one to two days are often required to obtain PCR results. This greatly limits the application of PCR in many areas of medicine and science and restricts the number of samples that can be analyzed. Faster thermal cyclers using hot air are available, but are not in widespread use because of difficulties in sample handling.

The recent emergence of new diseases such as AIDS and Lassa fever and the resurgence of old diseases such as tuberculosis and pneumonic plague increases the urgency for establishing a comprehensive system of international disease surveillance. Only PCR, with its ability to differentiate strains of viruses and bacteria and give detailed molecular information from small amounts of sample, has the capability of providing this information. Yet implementation of PCR testing of the scale required would be prohibitively expensive using the current technology. PCR with a high throughput capacity would provide benefit in many areas of public health, environmental monitoring, the food industries, and would permit wide scale screening for genetic diseases.

It would therefore be desirable to provide a molecular analyzer and method of use for the detection of specific molecules or specific parts of molecules in a sample, for example using PCR, that is capable of providing detailed molecular information from a small amount of sample.

It would also be desirable to provide a molecular analyzer and method of use that is capable of providing detailed molecular information in a short period of time.

It would further be desirable to provide a molecular analyzer and method of use that eliminates contamination of surrounding laboratory conditions.

It would further be desirable to provide a molecular analyzer and method of use that is less costly than current methods of detection.

It would further be desirable to provide a molecular analyzer and method of use that is less labor intensive than current methods of detection.

It would also be desirable to provide a molecular analyzer and method of use that provides sensitive detection of amplified DNA without the use of radioactive materials.

It would also be desirable to provide a molecular analyzer and method of use that is completely automated.

It would also be desirable to provide a molecular analyzer and method of use that is capable of providing high capacity detection of specific molecules or specific parts of molecules in a sample.

It would also be desirable to provide a molecular analyzer and method of use that is capable of accurately and rapidly controlling the temperature of a sample.

SUMMARY OF THE INVENTION

It is therefore an object of this invention to provide a molecular analyzer and method of use for the detection of specific molecules or specific parts of molecules in a sample, for example using PCR, that is capable of providing detailed molecular information from a small amount of sample.

It is a further object of this invention to provide a molecular analyzer and method of use that is capable of providing detailed molecular information in a short period of time.

It is also an object of this invention to provide a molecular analyzer and method of use that eliminates contamination of surrounding laboratory conditions.

It is also an object of this invention to provide a molecular analyzer and method of use that is less costly than current methods of detection.

It is further an object of this invention to provide a molecular analyzer and method of use that is less labor intensive than current methods of detection.

It is also an object of this invention to provide a molecular analyzer and method of use that provides for sensitive detection of amplified DNA without the use of radioactivity.

It is also an object of this invention to provide a molecular analyzer and method of use that is completely automated.

It is also an object of this invention provide a molecular analyzer and method of use that is capable of providing high capacity detection of specific molecules or specific parts of molecules in a sample.

It is also an object of this invention to provide a molecular analyzer and method of use that is capable of providing accurate and rapid temperature control of a sample.

These and other objects of the invention are accomplished in accordance with the principles of this invention by providing a molecular analyzer and method of use for sensitive, rapid and accurate detection of specific molecules or specific parts of molecules in a test sample to be detected without the use of radioisotopes. According to the present invention, a sample tube holder having at least one sample tube, the inner surfaces of which may be capable of specifically binding the molecules to be analyzed, may be comprised of a frame having elastomeric members fitted to it. The frame, or the elastomeric members, is provided with at least one internal chamber for holding a detection reagent and an evacuated chamber, both chambers being in communication with the at least one sample tube, for example by means of internal conduits. The sample tube holder is further provided with means for blocking and unblocking the internal conduits such that when the conduits are blocked, no communication between the at least one sample tube, the at least one internal chamber and the evacuated chamber occurs, and when the conduits are selectively unblocked, communication occurs, and reagents contained in the internal chambers are selectively drawn through the at least one sample tube and into the evacuated chamber without having allowed any molecules in the sample to have escaped into the atmosphere.

Alternatively, the sample tube holder may be comprised of a frame having elastomeric members having at least one sample tube sealingly held therebetween and having at least one pair of orifices for providing sealable access to the at least one sample tube. The frame is provided with at least one internal chamber for holding a detection reagent and an evacuated chamber, both chambers being in communication with the at least one sample tube. The sample and the detection reagents may be sequentially loaded through one of the at least one pair of orifices where they may be sequentially drawn through the at least one sample tube into the evacuated chamber and may be removed from the other of the at least one pair of orifices. The frame may additionally be provided with recesses such that the elastomeric members may be disposed within the recesses within the frame such that the elastomeric members and the at least one sample tube are together removable from the frame.

Alternatively, the sample tube holder may be comprised of a frame provided with elastomeric members having at least one sample tube sealingly held therebetween, and one of the elastomeric members provided with at least one internal chamber containing a detection reagent and the other of the elastomeric members having an evacuated chamber, with both the at least one internal chamber and the evacuated chamber being in communication by means of internal conduits with the at least one sample tube. The sample tube holder may be provided with means for sequentially blocking and unblocking the internal conduits, which may be comprised of hollow needles having end and side holes, such that when the internal conduits are blocked, no communication between the at least one internal chamber and the at least one sample tube occurs, and when the internal conduits are unblocked, communication occurs and the reagents are sequentially passed through the at least one sample tube into the evacuated chamber.

Alternatively, the sample tube holder may be comprised of a rigid frame having at least one sample tube sealingly held between opposing sides of the frame, a reagent chamber slidably engageable with one side of the frame and an evacuated chamber slidably engageable with the other side of the frame such that a fluid passageway is provided between the reagent chamber, the at least one sample tube and the evacuated chamber when the reagent chamber and the evacuated chamber are engaged with the frame. The frame may further be provided with at least one door hingedly attached to the frame for holding securely the at least one pair of ends of the at least one sample tube.

A molecular analyzer according to the present invention may also include a means for controlling the temperature of the test sample. A three-compartment air thermal controller is preferably provided, having a hot air compartment of recirculating hot air, a cold air compartment of recirculating cold air and a sample compartment of recirculating air and into which sample tubes are placed, with a rotatable door provided between the hot air compartment and the sample compartment, and a rotatable door provided between the cold air compartment and the sample compartment. Opening and closing the doors changes the air flow pathways between the three compartments. The doors may opened and closed so as to achieve temperatures in the sample compartment that are optimal for DNA polymerase activity and optimal for DNA annealing.

The sample compartment of the temperature controller is also preferably divided into an upper section and a lower section by a heat conductive base which holds any of the sample tube holders of the present invention, the lower section being maintained at the temperature of the cold air compartment. The reagents contained in the reagent chambers of the sample tube holder, which rests in the base, may thereby be maintained at the temperature of the cold air compartment.

A molecular analyzer of the present invention may also have means for detecting the presence or absence of at least one target molecule in a test sample, including the products of a molecular analysis, and further including the DNA products of a polymerase chain reaction, without the use of radioisotopes and without having to remove the test samples from the sample tubes. The chemiluminescence of a test sample may be measured by sequentially moving the sample tubes held in a sample tube holder into a carriage comprised of an upper section provided with a mirror, which is preferably a first-surface parabolic mirror, and a lower section provided with a lens such that light from the sample tube is reflected by the mirror into the lens, and is focused by the lens onto a detector element where photons are counted. The fluorescent emission of a test sample may be also measured by sequentially moving the sample tubes held in a sample tube holder between a mirror, which is preferably a first-surface parabolic mirror, and a lower section provided with a lens such that fluorescent emission from the sample tube is reflected by the mirror into the lens, and is focused by the lens onto a detector element.

BRIEF DESCRIPTION OF THE DRAWINGS

The above and other objects and advantages of the invention will be apparent from the following detailed description of the preferred embodiments, taken in conjunction with the accompanying drawings, in which like reference characters represent like elements throughout, and in which:

FIGS. 7A–C are sectional views of a sample tube holder of the present invention showing the detection of amplified DNA by chemiluminescence;

FIG. 9B is a sectional view of the sample tube holder shown in FIG. 9A, showing the mechanism for detection;

FIGS. 9C–E show the detection mechanism of the sample tube holder of FIGS. 9A and 9B;

FIGS. 11A–C are plan views of a preferred embodiment of a thermal controller of the present invention;

FIGS. 14A and 14B are partial views of a preferred method for detecting target molecules;

FIG. 15 is an isometric view of another preferred embodiment of a sample tube holder of the present invention;

FIG. 16 is a sectional view taken along line 16—16 of FIG. 15;

FIG. 17 is a sectional view taken along line 17—17 of FIG. 15;

FIG. 18 is a sectional view taken along line 17—17 of FIG. 15 of another preferred embodiment of the present invention;

DETAILED DESCRIPTION OF THE DRAWINGS

The molecular analyzer and methods of use according to the present invention are shown in FIGS. 1–26. The present invention is primarily described herein with reference to PCR; however, the apparatus and methods of the present invention are not limited to PCR, as will be understood by one of skill in the art.

Figure 1:
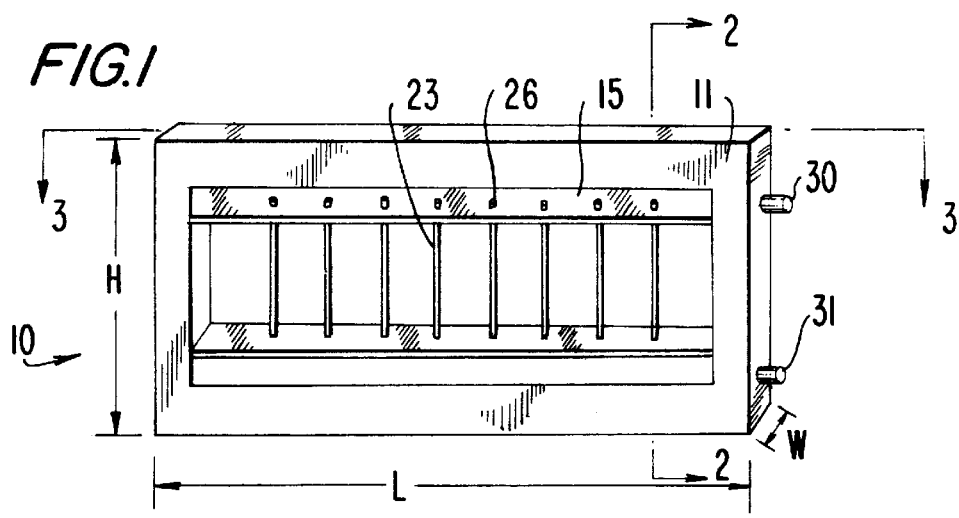
FIG. 1 shows a preferred embodiment of a sample tube holder of the present invention.

FIG. 1 shows a preferred embodiment of sample tube holder 10 of the molecular analyzer of the present invention. This embodiment of the present invention allows multiple liquid samples to be loaded into sample tube holder 10 for simultaneous treatment, such as thermal cycling, and also allows the products of a reaction to be detected without exposing the environment to molecules within the sample tube.

Sample tube holder 10 is preferably comprised of frame 11, which is preferably rectangular in shape and preferably has dimensions of approximately 10.2 centimeters (4.0 inches) in length L, 5.7 centimeters (2.25 inches) in height H, and 0.8 centimeters (0.3 inches) in width W. However, it will be understood that any size or configuration of frame 11 may be used in accordance with the present invention.

Figure 2:
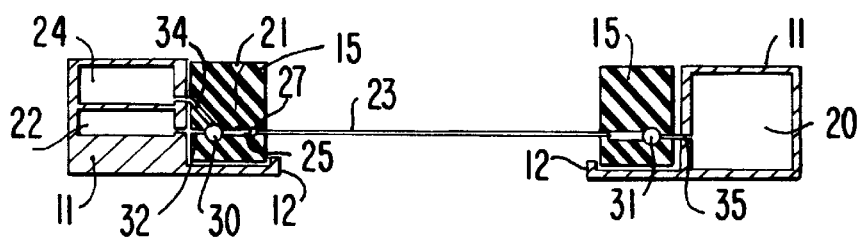
FIG. 2 is a cross-sectional view taken along line 2—2 of FIG. 1.

As shown in FIG. 2, frame 11 is provided with internal evacuated waste chamber 20 within the length L of one of its side members. Frame 11 is further provided with first and second internal reagent chambers 22, 24 within the length L of the other of the side members of frame 11. Alternatively, any or all of evacuated chamber 20 and internal reagent chambers 22, 24 may be provided within elastomeric members 15. Internal reagent chambers 22, 24 are filled with whichever detection reagents are suitable for the particular analysis being carried out. For example, if PCR is being carried out and it is desired to detect amplified DNA products by chemiluminescence, first internal reagent chamber 22 might contain a solution of alkaline phosphatase conjugate and second internal reagent chamber 24 might contain a solution of dioxetane. Any number of internal reagent chambers 22, 24 may be provided; the number and the contents of internal reagent chambers 22, 24 will be dependent upon the type of analysis being performed.

Sample tube holder 10 is further provided with a pair of oppositely disposed elastomeric members 15, preferably made from silicone rubber. Elastomeric members 15 are fitted closely to frame 11 as shown in FIGS. 1 and 2. For this purpose, frame 11 is provided with extensions 12, as shown in FIG. 2. Sample tubes 23, which are typically 10 microliter ReporterTubes™, extend between elastomeric members 15 and are sealingly engaged with elastomeric members 15 such that there exists a vacuum within each sample tube 23 prior to filling with liquid test sample. Preferably eight sample tubes 23 are contained in each sample tube holder 10, but any number of sample tubes 23 may be used.

Sample tubes 23 are preferably formed from glass or other transparent rigid material having molecules attached to their inner surfaces that are capable of binding target molecules in the test sample in a specific manner, thereby causing the target molecules to be bound to the inside surfaces of sample tubes 23.

A plurality of sample loading ports 26 is provided in one of elastomeric members 15. The number of sample loading ports 26 will be the same as the number of sample tubes 23 held. Sample loading ports 26 extend through elastomeric member 15 to form conduits into sample tube 23. Sample loading ports 26 may be provided with lips 27 and orifice 21, similar to those shown in FIGS. 4B and 5B.

Sample tubes 23 may be filled with liquid test sample to be evaluated as follows. Pipettor tips 118 of a multi-channel micropipettor 150 (see FIGS. 5A and 5B) are placed into vials or other containers that hold the liquid test sample. Pipettor tips 118 are filled with the liquid samples. Lips 27 and orifice 21 of sample loading ports 26 of sample tube holder 10 are formed so as to facilitate and guide pipettor tip 118 (see FIGS. 5A and 5B) in being placed and pressed down into orifice 21. The application of downward force will then cause pipettor tip 118 to puncture lips 27 and enter cavity 25, shown in FIG. 2, and similar to cavity 125 shown in FIG. 5B. The liquid sample contained in pipettor tip 118 will then be drawn by vacuum into sample tube 23.

Figure 3A:
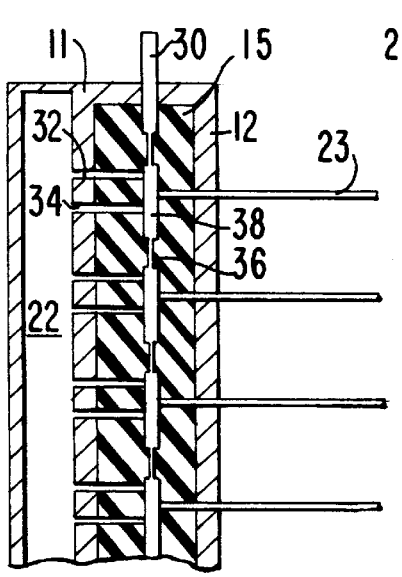
FIGS. 3A–C are cross-sectional views taken along line 3—3 of FIG. 1.
Figure 3B:
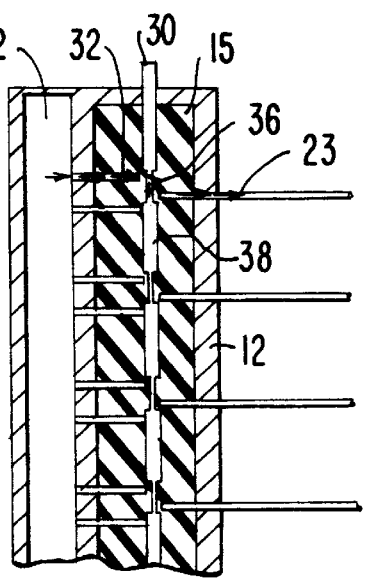
Figure 3C:
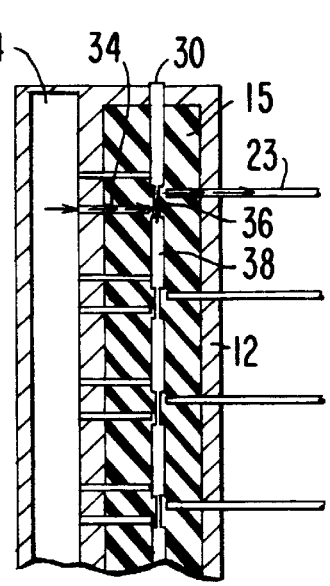

Sample tube holder 10 is also provided with first valve core rod 30 and second valve core rod 31. Valve core rods 30 and 31 extend lengthwise through elastomeric members 15, as shown in FIGS. 1–3. Valve core rods 30 and 31 are moveable in the direction of the length L of frame 11. Valve core rods 30 and 31 are provided with valve core rod solid portions 38 and valve core rod channel portions 36, as shown in FIGS. 3A–C. Valve core rod channel portions 36 are not solid and provide an open pathway between internal reagent chambers 22, 24 and sample tube 23.

As shown in FIG. 2, first reagent conduit 32 extends from first internal reagent chamber 22 through elastomeric member 15 until it reaches first valve core rod 30. Second reagent conduit 34 extends from second internal reagent chamber 22 until it reaches first valve core rod 30.

After sample tubes 23 have been filled with the liquid sample to be analyzed, and after amplification by thermal cycling, the reagents contained in internal reagent chambers 22, 24 must also be loaded into sample tubes 23 so detection of target molecules may be performed. The present invention permits sequential addition of the reagents contained in first internal reagent chamber 22 and second internal reagent chamber 24, without exposing either the reagents or the test sample to be analyzed to the atmosphere, in the following manner.

Prior to adding either of the reagents contained in internal reagent chambers 22, 24 to sample tubes 23, first valve core rod 30 is in the position shown in FIG. 3A. With first valve core rod 30 in this position, the solid portions 38 of first valve core rod 30 are in contact with first and second reagent conduits 32, 34. Thus, both first and second reagent conduits 32 and 34 are blocked, and neither of the reagents contained in internal reagent chambers 22, 24 is free to flow into sample tubes 23. Similarly, second valve core rod 31 blocks third conduit 35 to prevent connection between sample tube 23 and evacuated chamber 20.

After thermal cycling, when it is desired to add the first reagent to sample tubes 23, first valve core rod 30 is pushed to the position shown in FIG. 3B, and simultaneously second valve core rod 31 is pushed to a point at which third conduit 35 is unblocked and connection between sample tube 23 and evacuated chamber 20 occurs. At this position, valve core rod channel portions 36 communicate with first reagent conduit 32 to provide a pathway into sample tubes 23. The first reagent is then drawn by the vacuum in evacuated chamber 20 into sample tubes 23 in the direction of the arrows shown in FIG. 3B.

When it is desired to add the second reagent to sample tubes 23, first valve core rod 30 is pushed to the position shown in FIG. 3C. At this position, valve core rod channel portions 36 communicate with second reagent conduit 34 to provide a pathway into sample tubes 23. Second valve core rod 31 remains in a position at which third conduit 35 is unblocked. Thus, the second reagent is drawn by the vacuum in evacuated chamber 20 into sample tubes 23 in the direction of the arrows shown in FIG. 3C.

Valve core rods 30 and 31 provide a preferred means for blocking and unblocking first and second reagent conduits 32 and 34 and third conduit 35. It will be understood by those of skill in the art that various other means may be used for this purpose.

FIGS. 4A–5B show another embodiment of a sample tube holder 100 for use with the present invention. This type of sample tube holder 100 is particularly useful for carrying out PCR when it is necessary to recover amplified DNA products following thermal cycling, or for detecting other molecules when it is desired to recover such molecules for further use. This embodiment of the present invention allows multiple liquid test samples to be loaded at the same time, and is preferably comprised of frame 111 containing sample tubes 123 sealingly engaged with frame 111 such that there exists a vacuum within each sample tube 123 prior to filling sample tube 123 with test sample for evaluation. Each sample tube 123 may also be evacuated while retaining its vacuum. Frame 111 is preferably made of an elastomeric material, for example silicone rubber.

Figure 4A:
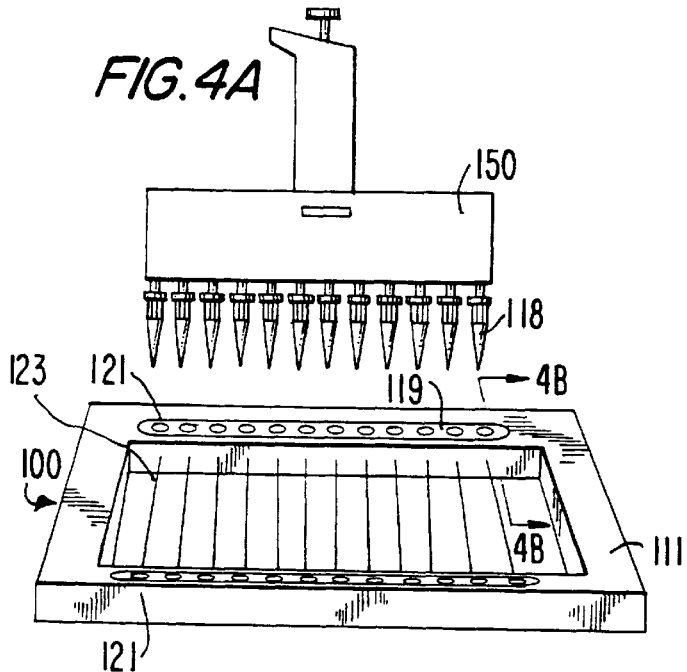
FIG. 4A is a projected view of another embodiment of a sample tube holder of the present invention.
Figure 4B:
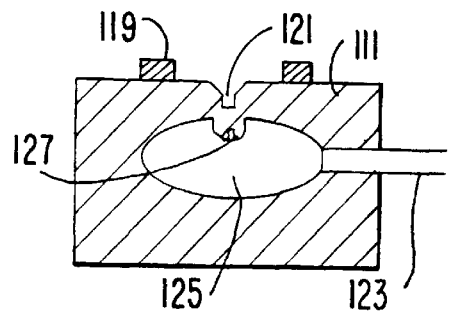
FIG. 4B is a sectional view taken along line 4B—4B of FIG. 4A.
Figure 5A:
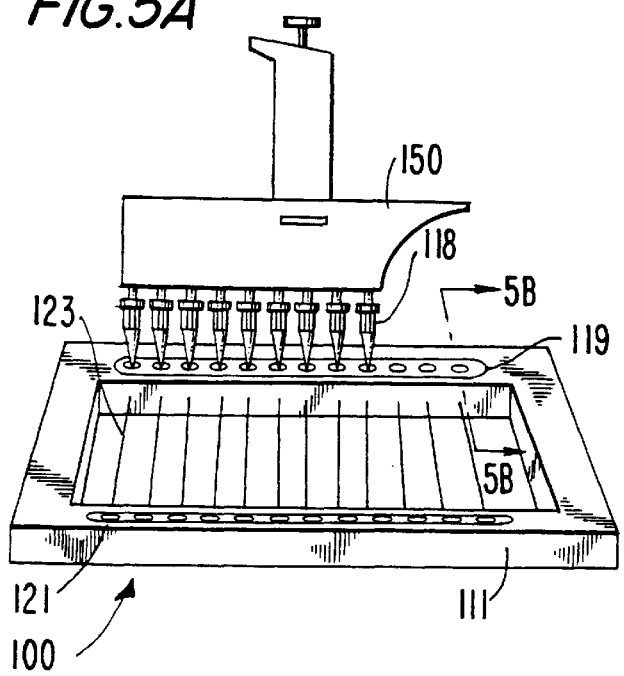
FIG. 5A shows the introduction of samples into the sample tube holder shown in FIG. 4A.
Figure 5B:
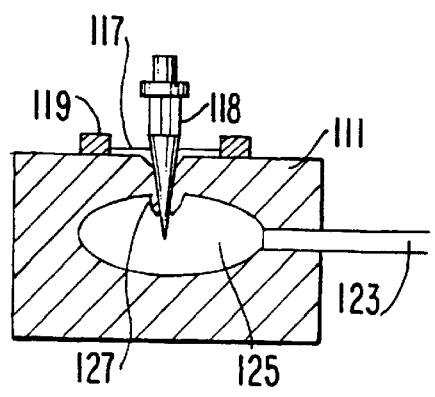
FIG. 5B is a sectional view taken along line 5B—5B of FIG. 5A.

Frame 111 has a plurality of cavities 125 formed within it, as shown in FIG. 4B. A cavity 125 is preferably positioned at the end of a sealed sample tube 123. Each cavity 125 may be formed with lips 127 and orifice 121, so formed as to guide pipettor tip 118 in being placed and pressed down into orifice 121, where an applied downward force will cause pipettor tip 118 to puncture lips 127 and enter cavity 125, as shown in FIG. 5B. If pipettor tip 118 contains a liquid sample, such liquid will at this time be drawn by vacuum into cavity 125 and sample tube 123. FIG. 5A shows a multi-channel micropipettor 150, in partial view, engaging each of its tips 118 in orifices 121.

As shown in FIGS. 4B and 5B, lips 127 are formed such that after tip 118 has been withdrawn, the entranceway created by the entry of tip 118 is closed and internal pressure that may build up within sample tube 123 will tend to seal the hole, preventing molecules from escaping.

After thermal cycling, it may be desirable to remove the liquid test samples from sample tubes 123, for example to purify the amplified DNA for use in other experiments. According to the present invention, after test samples have been thermal cycled, it is possible to remove the liquid samples from sample tubes 123 without exposing the atmosphere to contamination by molecules in the sample solution. A small amount of mineral oil is poured into each orifice 121, covering the surfaces of each orifice 121. A micropipettor 150 with multiple aerosol resistant tips 118 is used to introduce tips 118 into cavities 125 along one end of sample tubes 123. Tips 118 are released from micropipettor 150 and left in place, where they provide a filtered connection between sample tubes 123 and the atmosphere. Micropipettor 150 then is re-loaded with additional multiple aerosol resistant tips 118. The additional tips 118 are then pressed into orifices 121 which are located at the opposite ends of sample tubes 123, as shown in FIGS. 4A and 5A. Micropipettor 150 is then used to withdraw the contents of sample tubes 123 into tips 118. Since the opposing ends of sample tubes 123 are open there is no resistance to the samples being drawn out. Micropipettor 150 is then slowly lifted, and as tips 118 leave orifices 121 of sample tube holder 100, the layer of mineral oil 117, shown in FIG. 5B, ensures that no molecules from the sample solution may exit sample tube holder 123 and enter the atmosphere. Oil 117 coats the outside of pipettor tip 118 and as it is raised out of oil layer 117 the end of tip 118 is sealed by oil running down and collecting at its end. The contents of tips 118 may then be transferred to additional sample tubes or the wells of a microtiter plate that has been layered with oil, so that the aqueous sample is ejected beneath the oil. The transfer is completed by taking up a small amount of oil into each of the tips as they are being lifted from the sample wells so that the pipettor tips are sealed with oil before disposal.

A preferred method for sample removal that minimizes the risk of contamination by amplified DNA molecules makes use of a molded wall 119 that surrounds orifices 121, as shown in FIGS. 4B and 5B.

Figure 6A:
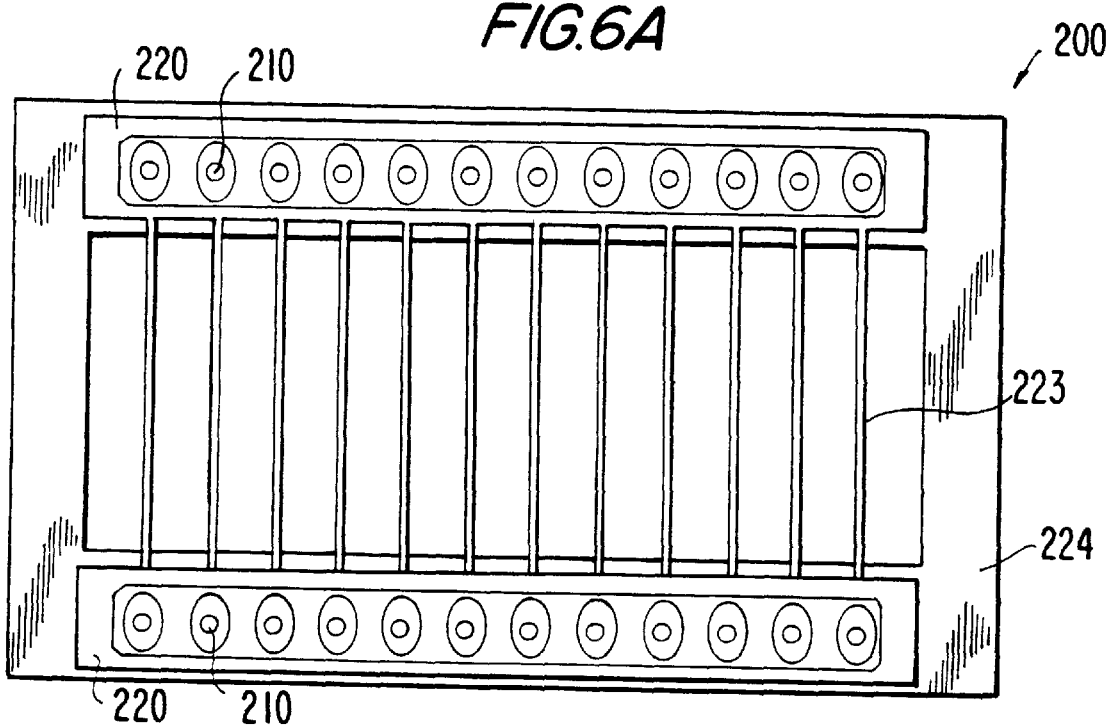
FIG. 6A is a plan view of another preferred embodiment of a sample tube holder of the present invention.
Figure 6B:
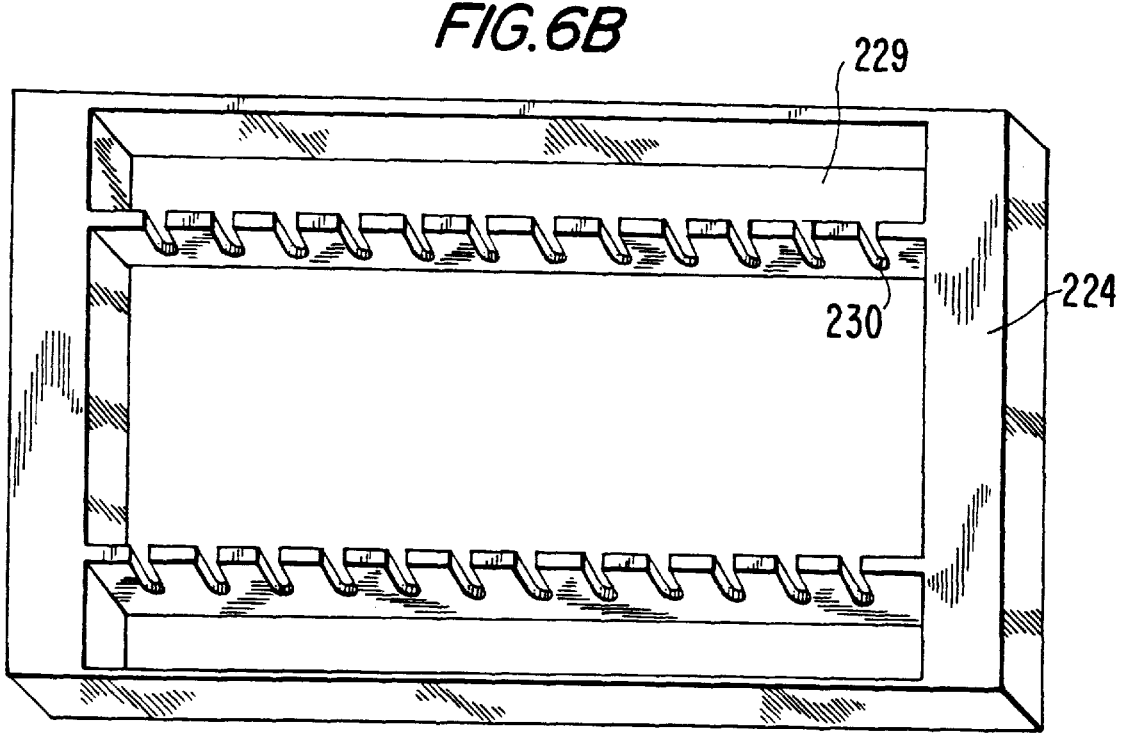
FIG. 6B is an isometric view of a portion of the sample tube holder shown in FIG. 6A.

FIGS. 6A and 6B show another embodiment of sample tube holder 200. In this embodiment, a pair of elastomeric strips 220 hold a multitude of sample tubes 223. Sample tubes 223 are held by elastomeric strips 220 at each of their ends, as shown in FIG. 6A. Orifices 210 provide access to sample tubes 223, as described previously.

Elastomeric strips 220 are held in rigid frame 224, which is typically formed from thermoplastic material. FIG. 6B shows rigid frame 224 without sample tubes 223 or elastomeric strips 220. Rigid frame 224 may be provided with recesses 229 to accommodate elastomeric strips 220. Rigid frame 224 may further be provided with openings 230 allow sample tubes 223 to pass in rigid frame 224.

FIGS. 7A–C show sectional views of a sample tube holder 300 particularly useful for detection of amplified DNA by chemiluminescence. Sample tube holder 300 is provided with frame 311, elastomeric members 333 and internal reagent chambers 331, 332 formed inside of one of elastomeric members 333. Internal reagent chambers 331 and 332 may contain reagents, for example to detect amplified DNA after thermal cycling, such as solutions of dioxetane and alkaline phosphatase conjugate, or for example to detect bound antigens in sample tube 323. Elastomeric members 333 sealingly hold sample tubes 323 between them. Sample tube holder 300 is further provided with evacuated chamber 320. Evacuated chamber 320 may be provided between frame 311 and the other of elastomeric members 333, which does not contain internal reagent chambers 331, 322. Evacuated chamber 320 may alternatively be provided in one of elastomeric members 333.

After sample tubes 323 have been filled with a liquid test sample and after thermal cycling, as described previously, the reagents contained in internal reagent chambers 331, 332 must be introduced into sample tubes 323. Hollow needles 334 and 335 provide a means for conveying the detection reagents contained in internal reagent chambers 331, 332 to sample tubes 323. In FIGS. 7A–C, needles 334, 335 are shown oriented at 90° to sample tubes 323; however, needles 334, 335 may be oriented parallel to sample tubes 323 or at any other desired or convenient angle. As shown in FIGS. 7A–C, this operation may be performed without exposing either the reagents or the liquid sample to the atmosphere, where contamination would be likely.

Hollow needles 334 and 335 are provided with end holes 339 at their ends 339A. Hollow needles 334 and 335 are further provided with side holes 338 at their sides 338A. When needles 334, 335 are pushed approximately 2 millimeters to the position shown in FIG. 7B, end holes 339 and side holes 338 provide a passageway for the reagent contained in chamber 332 flow into and through sample tube 323 and subsequently into evacuated chamber 320. The reagent contained in internal reagent chamber 332 first flows through side hole 338 of needle 334 a short distance through needle 334, then flows through end hole 339 of needle 334 into and through sample tube 323. The vacuum in evacuated chamber 320 draws the reagent contained in internal reagent chamber 332 through sample tube 323. Then, the reagent flows through end hole 339 of needle 335 an short distance through needle 335, and then out into evacuated chamber 320 through side hole 338 of needle 335.

For example, in a PCR analysis, a solution of alkaline phosphatase conjugated to streptavidin is contained in internal reagent chamber 332. Alkaline phosphatase solution washes unbound materials from sample tube 323 into evacuated chamber 320. Enzyme is captured by biotinylated amplimers bound to the inside of sample tube 323. In this manner unbound materials are washed out of sample tube 323 and molecules of amplified DNA are coupled with alkaline phosphatase enzyme.

After washing sample tubes 323 with the reagent contained in chamber 332, needles 334 and 335 are separately pushed into the positions indicated in FIG. 7C. First, needle 334 is pushed further into elastomeric member 333. Hole 339 of needle 334 provides a passageway for the reagent contained in chamber 331 to flow first a short distance through needle 334, then through side hole 338, and then into sample tube 323.

For example, in a PCR analysis, a dioxetane solution washes out unbound enzyme, which had previously been passed through sample tube 323, and fills sample tube 323.

While the second reagent that was contained in internal reagent chamber 332 is filling sample tube 323, needle 335 remains in the position shown in FIG. 7B.

After the washing out of unbound enzyme or other reagent that had previously been passed through sample tube 323, needle 335 moves into the position shown in FIG. 7C to seal off flow from sample tube 323 into evacuated chamber 320. The sealed sample tubes 323 are now ready for chemiluminescence measurements.

It will of course be understood by one of ordinary skill in the art that any other suitable means, for example valve core rods as described in connection with FIGS. 1–3, may be used to provide access to sample tubes 323 for reagents contained in internal reagent chambers 331, 332.

Figure 8:
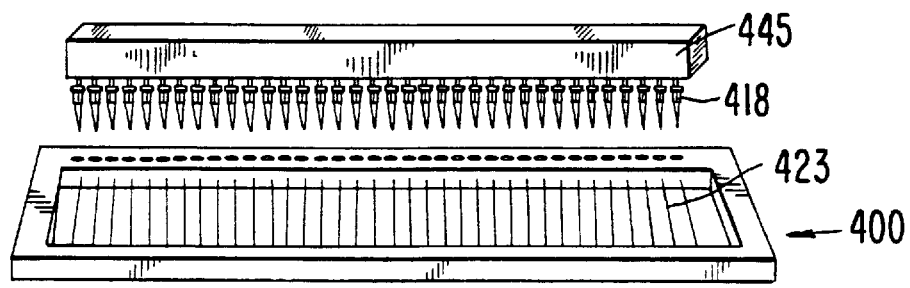
FIG. 8 shows a sample tube holder of the present invention containing multiple sample tubes and the introduction of samples into the sample tubes.

A molecular analyzer according to the present invention may employ a sample tube holder 400 having any number of sample tubes 423. For example, FIG. 8 shows a sample tube holder 400 having 36 sample tubes 423 that may be loaded using a 36-channel pipettor 445 having disposable tips 418. Such a pipettor 445 may be actuated by a robotic device (not shown), thereby loading or unloading 36 samples at a time.

Figure 9A:
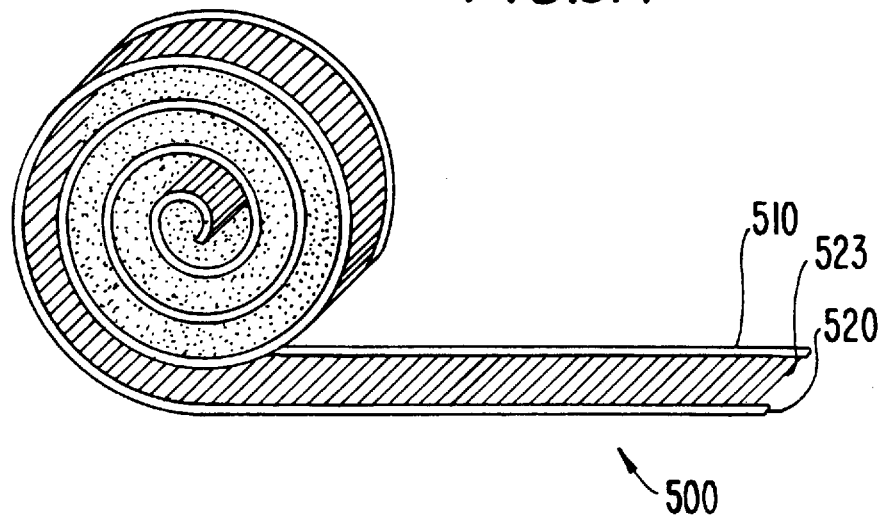
FIG. 9A shows another preferred embodiment of a sample tube holder of the present invention.

FIG. 9A shows another embodiment of sample tube holder 500 provided with two elastomeric members 510 and 520 having many sample tubes 523 sealingly held between them. Sample tube holder 500 may hold many thousands of sample tubes 523 as well as any number of internally contained detection reagents. Sample tube holder 500 may be rolled for convenient storage and dispensing, as shown in FIG. 9A.

FIG. 9B shows details of the continuous sample tube holder 500 assembly of FIG. 9A, including internal elements that provide for automated reagent delivery. First elastomeric member 510 is provided with orifices 521 and lips 527 by which liquid test samples may be loaded into evacuated cavities 525. The liquid sample is then drawn by vacuum into sample tubes 523, as previously described.

First elastomeric member 510 is further provided with first internal reagent chamber 522 and second internal reagent chamber 524. Internal reagent chambers 522, 524 may be filled with any detection reagent suitable for the analysis to be carried out. For example, if PCR is to be carried out, first internal reagent chamber 522 might contain a solution of alkaline phosphatase conjugate and second internal reagent chamber 524 might contain a solution of dioxetane. Any number of internal reagent chambers may be provided; the number and the contents of such chambers will be dependent upon the type of analysis being performed.

First elastomeric member 510 is also provided with first conduit 543 located between first and second internal reagent chambers 522, 524. First conduit 543 cooperates with sample tube 523 to provide a fluid connection between therebetween. First hollow needle 534 is also provided within first elastomeric member 510. First hollow needle 534 is provided with first needle side hole 534A. First needle side hole 534A permits fluid communication between first internal reagent chamber 522 and first conduit 543, and also between second internal reagent chamber 524 and first conduit 543, as will be described in greater detail below.

Second elastomeric member 520 is provided with internal evacuated chamber 540. Evacuated chamber 540 has as large a volume as is practicable within second elastomeric member 520, because it is the motor pulling provided by the vacuum contained within evacuated chamber 540 that causes the reagents to flow through sample tubes 523.

Second elastomeric member 520 is also provided with second conduit 545, which is located so as to have surrounding segments of second elastomeric member 520 between it and evacuated chamber 540, which allows for selective cooperation between sample tubes 523 and evacuated chamber 540. Second conduit 545 cooperates with sample tube 523 to provide a fluid connection therebetween. Second hollow needle 535 is also provided within second elastomeric member 520. Second hollow needle 535 is provided with second needle side hole 535A. Second needle side hole 535A permits fluid communication between internal evacuated chamber 540 and second conduit 545, as will be described in greater detail below.

FIGS. 9C–D show the embodiment of the sample tube holder shown in FIGS. 9A and 9B in connection with a method for automated quantitation of analysis after thermal cycling. This embodiment is preferred for use when millions of samples per year are to be analyzed using PCR, such as for blood testing, clinical diagnostics, disease surveillance and environmental tests.

FIGS. 9C–D show a transport frame comprised of first and second transport frame members 552, 554. The transport frame may be a component of a sample reading device (not shown). First transport frame member 552 surrounds first elastomeric member 510, and second transport frame member 554 surrounds second elastomeric member 520. First pair of internal rollers 562 are provided within first transport frame member 552 generally in the region surrounding internal reagent chambers 522, 524. Second pair of internal rollers 564 are provided within second transport frame member 554 generally in the region surrounding internal evacuated chamber 540.

Just after thermal cycling, when sample tube holder 500 enters a sample tube reading device (not shown), the relative positions of first and second internal rollers 562, 564, first and second elastomeric members 510, 520 and first and second needles 534, 535 are as shown in FIG. 9C. First and second needles 534 and 535 have not yet contacted either first conduit 543 or second conduit 545, and accordingly no reagents from either first or second internal reagent chamber 522 or 524 have entered sample tube 523.

Next, first and second pairs of internal rollers 562, 564 descend into the positions shown in FIG. 9D. First pair of internal rollers 562 have descended into a position in which first elastomeric member 510 is compressed to the point at which first needle 534 contacts first conduit 543. Second internal rollers 564 have descended into a position in which second elastomeric member 520 is compressed to the point at which second needle 535 contacts second conduit 545.

First needle side hole 534A provides a fluid pathway for the first reagent contained in first internal reagent chamber 522 to flow through first conduit 522 into sample tube 523. The first reagent is drawn through first conduit 543 through sample tube 523 and through second conduit 545 into evacuated chamber 540 by the vacuum in evacuated chamber 540. Second needle side hole 535A provides a fluid pathway for the first reagent, along with the unbound molecules that have been washed from sample tube 523 by the first reagent, to flow into evacuated chamber 540. For example, in a PCR analysis, alkaline phosphatase conjugate solution washes unbound molecules from sample tube 523 and binds to amplified DNA hybridized to immobilized probes within sample tube 523.

Next, after the first reagent has passed through sample tube 523, first and second internal rollers 562, 564 descend into the positions shown in shown in FIG. 9E. First pair of internal rollers 562 have further descended into a position such that first elastomeric member 510 is further compressed to the point at which first needle 534 contacts second internal reagent chamber 524. First needle side hole 534A provides a fluid pathway for the second reagent contained in second internal reagent chamber 524 to flow through first conduit 543 into sample tube 523. The second reagent is drawn through first conduit 543 through sample tube 523 and through second conduit 545 into evacuated chamber 540 by the vacuum in evacuated chamber 540. For example, in a PCR analysis, dioxetane substrate solution washes unbound out unbound enzyme from sample tube 523 and fills sample tube 523.

After the unbound molecules have been washed out of sample tube 523 and into evacuated chamber 540, second internal rollers 564 retract and return to their original positions, thus sealing off the flow of substrate from sample tube 523. It will be appreciated by those of skill in the art that means other than the hollow needles described above may be used to provide fluid pathways for reagent flow.

Figure 10:
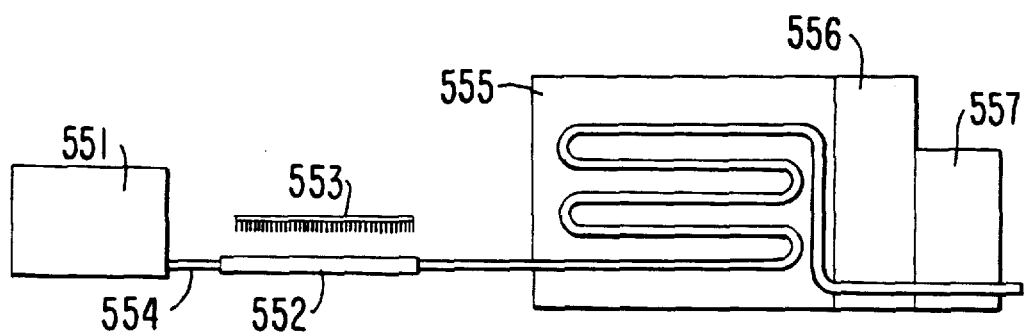
FIG. 10 shows a preferred embodiment of the present invention particularly suitable for high volume use.

FIG. 10 shows an embodiment of the present invention preferred for high volume analysis. A sample tube holder 500, rolled and containing thousands of sample tubes 523, as shown in FIG. 9A, may be stored in dispenser 551. Sample tube holder 500 is fed along track 554 into a sample loading station 552, where a multichannel pipettor 553 loads the samples to be analyzed into sample tubes 523, much like the process shown in FIG. 8. The loaded sample tubes 523 enter an air thermal controller 555 and are subjected to thermal cycling. Following the last cycle of amplification, sample tubes 523 enter an amplimer fixation compartment 556, in which amplified DNA in sample tubes 523 is annealed to hybridization probes attached to the inner surfaces of sample tubes 523. The protocol that is followed is determined by the type of analysis to be carried out and may include a preliminary manipulation of temperature of the sample solutions to denature or inactivate the DNA polymerase enzyme before following a temperature protocol that selects for maximum binding of amplimer to hybridization probes and binding of DNA polymerase to primed amplimer without permitting DNA extension to occur. The bound enzyme may then be used to amplify the signal of the amplified DNA by providing a substrate for affinity based detection reagents. After amplimer fixation, sample tubes 523 next pass into sample tube reader 557, where needles are pressed into sample tube holders 550 or any other means is used to wash out unbound molecules from sample tubes 523, and to add reagents, before detecting the bound DNA.

FIGS. 11A–C show a preferred embodiment of a thermal controller 40 for thermal cycling, or any other desired temperature manipulation, of the test sample contained in sample tubes 23 of the present invention. Hot air compartment 60 recirculates air at an elevated temperature, typically 200° C., by means of first fan 61 which forces the air around first central wall 62 and through heating element 63. Cold air compartment 70 recirculates air at a low temperature, typically 0° C., by means of second fan 71 which forces the air around second central wall 72 and through cooling element 73. Air is recirculated within sample compartment 80 by means of multi-blade turbine fan 81 which forces the air through sample tube holders 10, or any of the other embodiments of the sample tube holder of the present invention, and around third central wall 83.

Thermal controller 40 is also provided with doors 90 and 91, which may be moved between closed positions and any degree of open positions. Doors 90 and 91 work cooperatively to control the temperature of air in sample compartment 60. Doors 90 and 91 may be rotated by a servo mechanism (not shown) directed by microprocessor control. For example, the microprocessor may use information about the temperature at various locations in thermal controller 40 to calculate whether either door 90 or door 91 should be opened as well as the degree to which either doors 90 or door 91 should be opened in order to carry out as exactly as possible a protocol which has been entered for temperature control of test samples contained in sample tubes 23.

FIG. 11B shows the flow of air in the thermal controller 40 after first door 90 has been opened. Hot air from hot air compartment 60 enters sample compartment 80 in the direction of the arrows labelled "H" where it is drawn into multi-blade turbine fan 81. Multi-blade fan 81 combines and mixes streams of air at different temperatures that enter it before forcing the blended air to contact sample tubes 23 held in sample tube holder 10. Air from sample compartment 80 exits sample compartment 80 and enters hot air compartment 60 in the direction of the arrows labelled "S."

Similarly, air from cold air compartment 70 may enter sample compartment 80 when second door 91 is rotated, as shown in FIG. 11C. Cold air from cold air compartment 70 enters sample compartment 80 in the direction of the arrows labelled "C" where it is drawn into multi-blade turbine fan 81. Air from sample compartment 80 exits sample compartment 80 and enters cold air compartment 70 in the direction of the arrows labelled "S."

The configuration of thermal controller 40 of the present invention permits rapid rates of temperature change of sample solutions contained in sample tubes 23. As a result, movements from elongation to denaturation and annealing temperatures are virtually instantaneous. Thus, reaction cycle times are minimized and the highest degree of DNA target specificity and amplified product yield is obtained. In addition, rapid cooling of a sample after a PCR amplification provides a means for trapping target molecules on the inside surface of a sample tube before detection by chemiluminescence, fluorimetry or other techniques. Rapid temperature transitions also dramatically reduce false priming.

To maximize cost effectiveness and productivity, PCR sample solutions should spend as much time as possible at optimal polymerase extension temperatures with as brief as possible interventions for transits to denaturation and annealing temperatures. For example, door movements of thermal controller 40 of the present invention during a ten second PCR thermal cycle will be described. A record of the temperature changes recorded in a sample tube 23 of thermal controller 40 during such a ten second thermal cycle is shown in FIG. 13B. Sample tube holder 10 containing sample tubes 23 are loaded into sample compartment 80. The air in third sample compartment 80 is maintained between 72° C. and 78° C. The air in hot air compartment 60 is maintained at 200° C. The air in cold air compartment 70 is maintained at 0° C.

When first door 90 is opened, hot air at 200° C. from hot air compartment 60 flows into sample compartment 80 while at the same time air at 72°–78° C. from sample compartment 80 flows into hot air compartment 60. The net effect is that the temperature of the air in sample compartment 80 is rapidly raised. Measurements of temperature are used by thermal controller 40 to calculate the degree to which door 90 should be opened, and the time for its complete closing in order that a final target temperature is reached, in the present example, that of 96°–97° C., at which temperature DNA present in the test sample is instantaneously denatured.

The temperature of the solution may now be lowered rapidly to an optimum annealing temperature by opening second door 91. Cold air at 0° C. from cold air compartment 70 flows into sample compartment 80 while at the same time air at 96° C. from sample compartment flows into cold air compartment 70. By this means the temperature of the air in sample compartment 80 may be lowered rapidly from 96° C. to 54° C., or to another optimal temperature at which annealing of primers to template DNA occurs. Annealing may occur virtually instantaneously or may require a few seconds.

Annealing may occur virtually instantaneously or may require a few seconds. The thermal controller 40 of the present invention is able to maintain sample temperatures at any desired temperature with great precision by opening first door 90 or second door 91, as required, to admit small quantums of hot air or cold air to sample compartment 80, the quantity of added hot or cold air being calculated by the microprocessor and software based on temperature measurements continuously being made in sample compartment 80.

After annealing has occurred, first door 90 is again opened. Air at 200° C. from hot air compartment 60 flows into sample compartment 80 while air at 54° C. from sample compartment 80 flows into hot air compartment 60. The net effect is that the temperature of the air in sample compartment 80 is raised to 78° C., or another optimum temperature for polymerase extension of the annealed primer. The length of time required for extension depends mainly on the length of the amplified DNA that is to be made and the sequence of the DNA. Taq polymerase, for example, incorporates nucleotide bases at a rate of 30 to 80 bases per second. After allowing a sufficient time for extension, each strand of the original double-stranded DNA molecule has been duplicated and the thermal cycling process may be repeated typically for 30 to 50 rounds.

Figure 12:
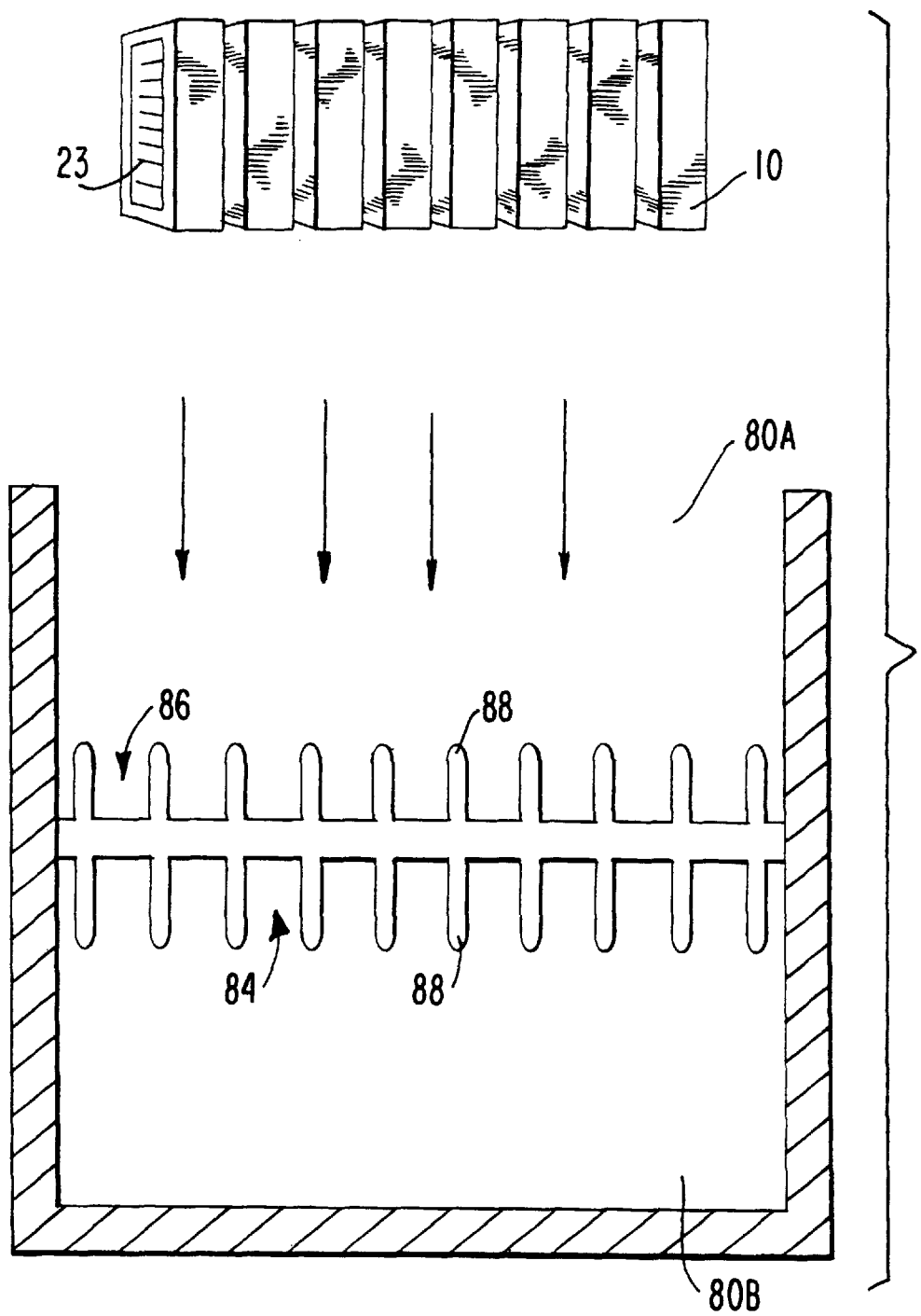
FIG. 12 is a sectional view of a portion of the thermal controller shown in FIGS. 11A–C.

The configuration of thermal controller 40 of the present invention also permits the detection reagents contained with internal reagent chambers 22, 24 of sample tube holders 10, or any of the other sample tube holders described herein, to be kept cool during thermal cycling or other temperature manipulation. This is advantageous because certain preferred detection reagents, such as alkaline phosphatase or other enzymes and organic reagents are unstable at high temperatures. These reagents should preferably be maintained at room temperature, or below, for stability. For this purpose, sample compartment 80 of thermal controller 40 is preferably provided with base 84, which is shown in FIG. 12. Base 84 is preferably made from a highly conductive metal, for example aluminum. Base 84 is provided with spaces 86 in which to receive sample tube holders 10. Sample tube holders 10 rest in spaces 86 during thermal cycling. Base 84 is also provided with fins 88, which aid in improving the efficiency of cooling sample tube holders 10.

Aluminum base 84 effectively divides sample compartment 80 into a first section 80A and a second section 80B. Only first section 80A is exposed to hot air from hot air compartment 60 when door 90 is opened. Second section 80B is kept cold at all times by the refrigerated air from cold air compartment 70. Therefore, aluminum base 84 and the detection reagents contained within sample tube holder 10 are kept cool while sample tubes 23 are exposed to hot air during thermal cycling.

Figure 13A:
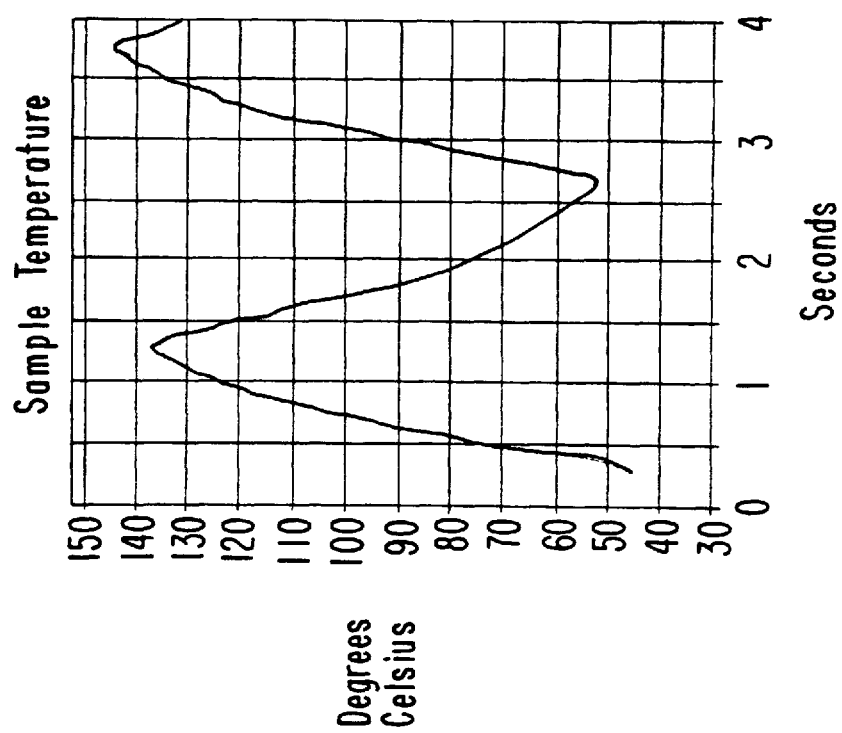
FIGS. 13A, 13A' and 13B are recordings of temperatures made within the thermal controller shown in FIGS. 11 and 12 and within a sample tube.
Figure 13A:
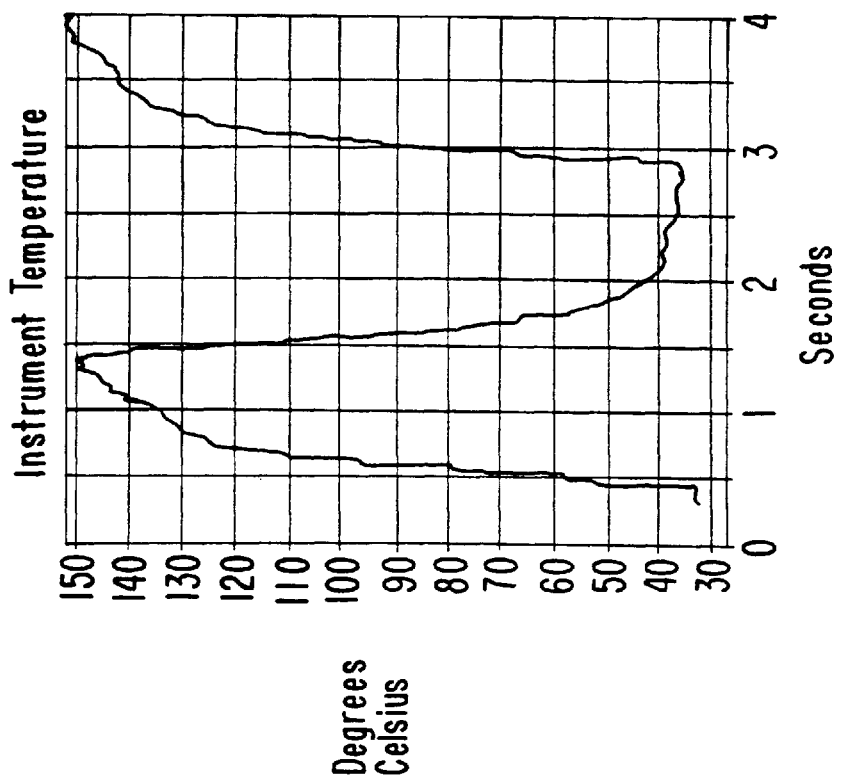
Figure 13B:
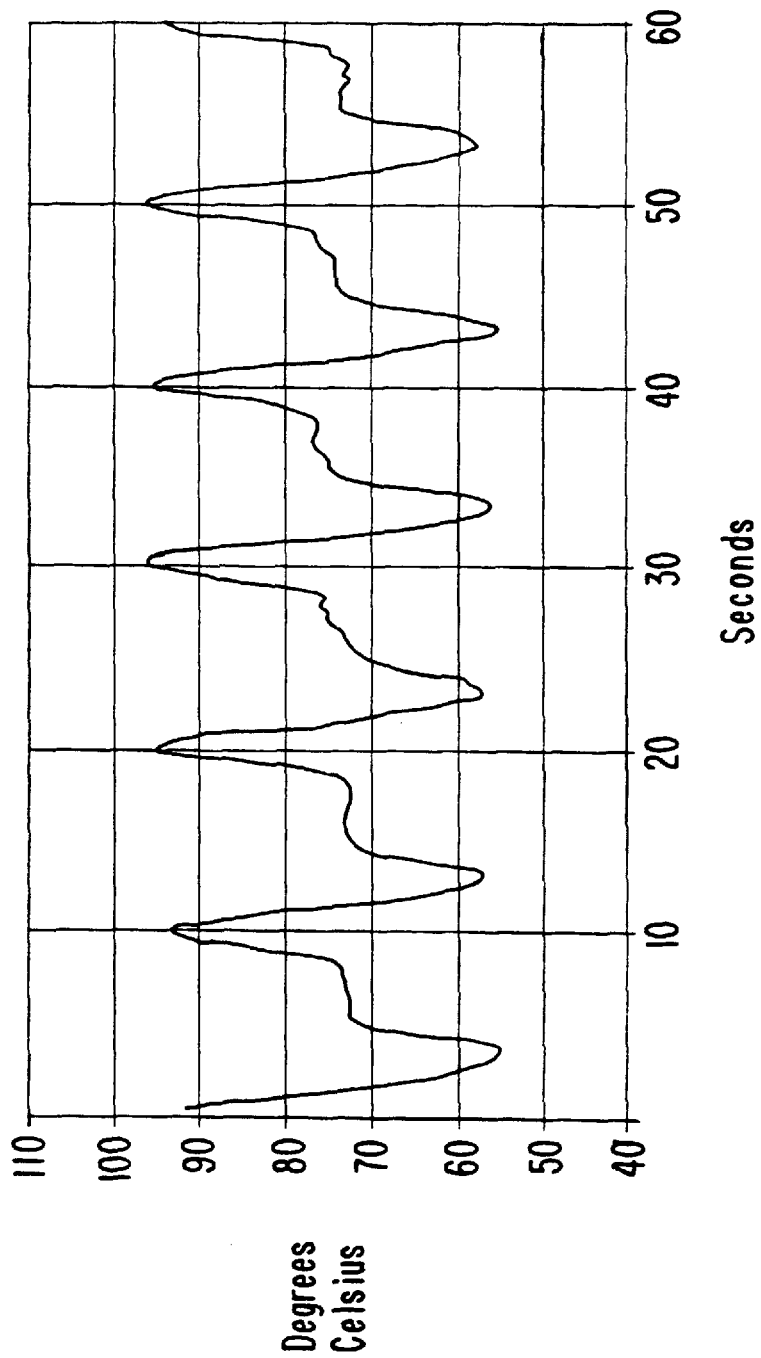

FIGS. 13A and 13A' show data obtained from an air thermal controller 40 of the present invention. Preferably, thermal controller 40 induces temperature changes of 200° C. per second, within the temperature range of 50° C. and 100° C., in sample solutions contained in sample tubes 23 in thermal controller 40. It will, of course, be understood that thermal controller 40 is capable of providing any desired temperature changes within any desired temperature range simply by adjusting the temperatures within hot air compartment 60 and cold air compartment 70 and by regulating the rates at which first and second doors 90 and 91 are opened. FIG. 13B is a recording of temperature changes within a sample tube 23 induced by a thermal controller 40 of the present invention that shows the rapid thermal transitions that may be achieved between denaturation, annealing and elongation temperatures for amplification of DNA using PCR.

After thermal cycling, amplimers are captured by hybridization probes that have been covalently attached to the inside surfaces of sample tubes 23. These probes do not interfere with PCR amplification since any amplimers that may be bound by probes during the annealing step are pushed off by the DNA polymerase during the extension reaction. After the final amplification, the solutions may be briefly raised to 130° C. in order to destroy DNA polymerase activity before incubating the solutions at an optimum annealing temperature for capture of amplimers by bound probes. Alternatively, the solutions may be taken to denaturation temperature and then rapidly brought below 20° C. Single stranded DNA forms stable hybrids with probes at this temperature; however, the DNA polymerase is not active and does not remove the target DNA from its probe or the wall of sample tube 23.

Figure 24:
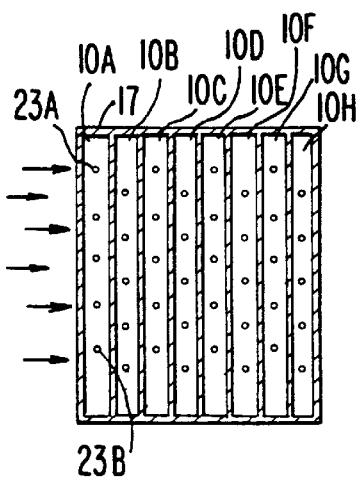
FIG. 24 is a sectional view of a group of sample tube holders held in a rack, taken horizontally across the mid-portion of the rack.

FIG. 24 shows a preferred arrangement of sample tubes 23 for thermal cycling. FIG. 24 is a section view of a bounding container 17 holding a group of sample tube holders 10A–H, taken horizontally across the across the mid-portions of sample tubes 23 held by sample tube holders 10A–H. It will be understood that the arrangement shown in FIG. 24 is viable for all embodiments of sample tube holders of the present invention that are described herein. Each row of sample tubes 23 contained in holders 10A–H is offset from the other. This may be accomplished by using sample tube holders 10 that have the sample tubes 23 held non-symmetrically. Thus, the distance between the first tube 23A of sample tube holder 10A and the end of bounding container 17 is less than the distance between the last sample tube 23B of sample tube holder 10A and the opposite end of boundary container 17. This permits the preferred configuration to be achieved by rotating alternating sample tube holders 10 in bounding container 17. Sample tube holders 10B, 10D, 10F, and 10H have been rotated 180° with respect to sample tube holders 10A, 10C, 10E and 10G so that the distances between sample tubes 23 and sample tube holders 10A–H are reversed. The result is that neighboring sample tubes 23 contained within boundary container 17 are not aligned but are spaced equidistant from each other, thus maximizing airflow around each sample tube 23. The arrows show the direction of air flowing around sample tubes 23 within temperature controller 40 for thermal cycling. The offsetting of sample tubes 23 with respect to one another may alternatively be accomplished by staggering alternate sample tube holders 10 (not shown).

Many methods for detection of target molecules within a sample tube 23 of the present invention following thermal cycling may be employed using the apparatus of the present invention. A preferred method for detection by chemiluminescence is shown in FIGS. 14A–B. According to this method, after detection reagents have been introduced to sample tubes 23 held in sample tube holder 10, or any of the other sample tube holders described herein, sample tube holder 10 is placed in carriage 800 of a sample reading compartment (not shown), where photons are counted for each sample tube 23. Carriage 800 is comprised of upper section 810 and lower section 820. Upper section 810 contains a mirror 830. Mirror 830 is preferably a first-surface parabolic mirror preferably 1 inch×0.0250 inches to match the dimensions of the preferred embodiment of sample tube holder 10 shown in FIGS. 1–3. Lower section 820 of carriage 800 contains a lens 840, which is preferably a convex or bi-convex lens. Located beneath lens 840 at the focal point of lens 840 is detection element 850 of digital photomultiplier tube 852.

Sample tube holder 10 is positioned between first and second sections 810, 820 such that a sample tube 23 held in sample tube holder 10 is between mirror 830 and lens 840, as shown in FIG. 14A. Then, mirror 830 descends into the position for reading of chemiluminescence shown in FIG. 14B, where sample tube 23 is located in between mirror 830 and lens 840 such that mirror 830 reflects chemiluminescent light from sample tube 23 into lens 840. If mirror 830 is a parabolic mirror 830, sample tube 23 is located within the focus of parabolic mirror 830. Photons emitted from the sample in sample tube 23 are reflected by mirror 830 into lens 840 and focused onto detector element 850 of digital photomultiplier tube 852, which allows them to be counted. When carriage 800 is in the position shown in FIG. 14B, first and second sections 810 and 820 are closely fitted so as to exclude external light, including that from adjacent sample tubes 23, so that the readings obtained are exclusively of light emitted from the sample tube being read.

After the time chosen to take a photon count has elapsed, mirror 830 is withdrawn to the position shown in FIG. 14A. The length of time chosen for counting photons depends on a number of factors, including the sensitivity required, the particular enzymes and substrates that are used and the method of measurement chosen. Typically, the luminance of a chemiluminescent reaction increases linearly at a rate proportional to the amount of enzyme present until a plateau region is reached. The rate of increase of luminance during the initial period of linear increase may be determined by taking periodic readings of sample tube 23. The rate of increase in luminance that may be calculated from these measurements, known as "dynamic readings," provides a more accurate measure of chemiluminescence than single point determinations made after the passage of a set period of time.

Then the next sample tube 23 held in sample tube holder 10 is moved between first and second sections 810 and 820, and the process of reading photons is repeated for that sample tube 23. This procedure is repeated for each sample tube 23 held in sample tube holder 10.

A preferred embodiment of a sample tube reader (not shown) utilizes a carousel dispensing device that holds up to 12 sample tube holders 10, which are successively placed in carriage 800 for photon counting, whereby multiple readings on each sample tube 23 can be made. Typically, 5 seconds for each sample tube 23 is required for photon counting.

Figure 25:
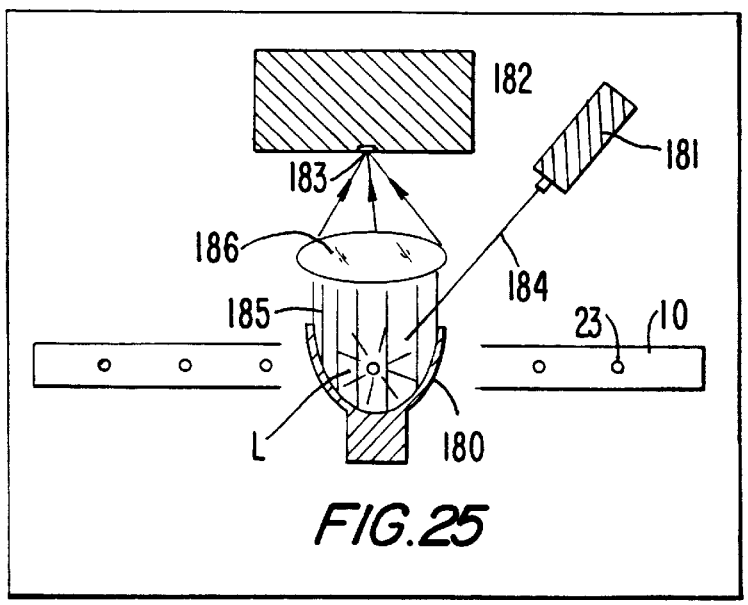
FIG. 25 is a schematic diagram of a preferred embodiment of a detection means according to the present invention.

FIG. 25 is a schematic diagram showing another preferred means for detecting the presence or absence of substances by fluorimetry in a sample tube 23. A fragmentary section of sample tubes 23 is shown against a background of sample tube holder 10. An elongated mirror 180 that has means of moving (not shown) into the space surrounded by a sample tube 23 and has means of locating (not shown) itself with respect to a sample tube 23 so that sample tube 23 is placed between mirror 180 and lens 186. Preferably, mirror 180 has the curvature of a parabola. Mirror 180, if a parabolic mirror, is moved so as to place sample tube 23 within the focus of the parabola. Fluorescent substances that may be present in a sample tube 23 may be detected by illuminating the sample tube 23 with stimulating light 184 from light source 181, preferably a laser. Fluorescent emission, indicated by radial lines "L" around sample tube 23, is reflected in a collimated manner 185 by mirror 180 into lens 186, which focuses light 184 into the detector element 183, where measurements are made.

It will be understood that many detection schemes are possible using the apparatus and methods of the present invention. For example, modifications of the arrangement shown in FIG. 25 may be used without laser 181 to measure scintillation emission, or chemiluminescence, or to measure the amount of light absorption at a particular wavelength by a solution in sample tube 23.

Another example of chemiluminescent detection of target DNA molecules after PCR amplification within a sample tube of the present invention will now be described. In this case, primers are incorporated into double stranded DNA during the PCR amplification. The DNA primers are 5' labelled with biotin, digoxigenin, or another label. Double stranded DNA is denatured to obtain single strands of DNA which may then be captured using hybridization probes having a sequence complimentary to an interior portion of the amplified product sequence.

After thermal cycling and attachment of amplimers to the inside surfaces of sample tubes, the two solutions stored in the sample tube holder are used sequentially. First, all unbound molecules are washed out of the sample tube by a solution containing alkaline phosphatase conjugated to streptavidin, if biotinylated primers were used, or to anti-digoxigenin antibody if the primers were labelled with digoxigenin. It will of course be understood by one those skill in the art that detection enzymes may be attached to amplimers using other means, such as enzyme-antibody conjugates with primers labelled with a wide variety of epitope molecules, or by using complimentary pairs of DNA or RNA molecules. Unbound enzyme is then washed out using a solution that contains dioxetane or another chemiluminescent substrate and readings are taken of the chemiluminescence produced by the catalytic interaction of the substrate with the surface bound enzyme. After readings have been taken the sample tube holder is disposed of, without having opened sample tubes or exposing the environment to amplified DNA products.

As another example, fluorometric detection of DNA target molecules after PCR amplification within a sample tube of the present invention may also be employed using the apparatus of the present invention. In this case, primers labelled with fluorescent tags or with rare earth chelator groups are incorporated into double stranded DNA during the PCR amplification. Double stranded DNA is denatured to obtain single strands of DNA which may then be captured using DNA probes having a sequence complimentary to an interior portion of the amplified product sequence.

After thermal cycling, amplified DNA is captured by the glass-bound probes. Only those amplified products that hybridize to the probes will be detected. A wash solution that may contain Eu+++ or Sm+++ if chelator groups have been used, which is stored in one of the reagent chambers in the sample tube holder is then used to wash all unbound molecules into an evacuated chamber in the sample tube holder before quantitating amplimers by fluorescence or by time-resolved fluorimetry.

As a further example, $^{32}p$ labelling to detect DNA target molecules after PCR amplification within a sample tube of the present invention may also be employed using the apparatus of the present invention. In this case, the PCR is carried out using a $^{32}p$ dNTP, such as $\alpha^{32}P$ thymidine 5'-triphosphate, which is incorporated into double stranded DNA during the PCR amplification. After thermal cycling, amplified DNA that has incorporated $^{32}P$ is hybridized to probes. Only those amplified products that hybridize to the probes will be detected. Scintillation fluid, stored in a chamber in the sample tube holder, is then used to wash out all unbound molecules and to detect captured products within the sample tubes. Readings are taken on each tube using a quantitative photon counter. Amplified products may then be quantitated by reference to a standard curve. After readings have been taken, the sample tube holder is disposed of, without having opened sample tubes or exposed the environment to amplified DNA products.

As a further example, detection of target molecules within a sample tube of the present invention using monoclonal antibodies may also be employed using the apparatus of the present invention. In this case, monoclonal antibodies that recognize the substance that is to be measured are first chemically attached to the inner surfaces of the sample tubes, before the sample tubes are assembled in the sample tube holder. Sample solutions containing unknown quantities of target molecules are passed through the sample tubes held in their sample tube holders. Afterwards, the sample tube holders are processed in a reader that washes out unbound molecules and reacts bound target molecules with a detection reagent, such as alkaline phosphatase conjugated to a second antibody recognizing the target. Unbound enzyme is then washed out by a solution containing the substrate, and the tube is sealed and read.

After attachment of target molecules to the inside surfaces of sample tubes, one to two solutions stored in chambers in the sample tube holders may be used sequentially, depending on the method of detection to be used. Sample tubes containing bound target molecules other than DNA or RNA may be processed automatically in the same instrumentation that is used to process samples following the PCR reaction. This method for detecting the presence of pathogenic organisms may be preferred since quantitation is made without opening the sample tubes or exposing the environment to the tube contents. Following quantitation, the sample tube holder and sealed sample tubes, which may contain infectious agents, may be safely discarded.

FIG. 15 shows another embodiment of a sample tube holder 400 that may contain a multitude of sample tubes 423. Sample tubes 423 span the width of frame member 410 of sample tube holder 400 and are sealingly joined with frame member 410. Ends 428, 429 of sample tubes 423 are connected by internal piping 444 (shown in dashed lines in FIG. 15) to first, second and third ports 421, 422, and 424 formed in sample tube holder 400. First and second ports 421 and 422 provide connection pathways between sample tube holders 423 and the atmosphere, while third ports 424 provide connection pathways between sample tubes 423 and evacuated space 450 of hollow block 430.

FIG. 17 is a sectional view taken along line 17—17 of FIG. 15. FIG. 17 shows the internal connections between sample tube 423 and ports 421, 422. Elastomeric tube holders 439 provide a means of sealing between sample tube 423 and frame member 410.

The face of each port 421, 422, 424 is sealed by an elastomeric pad 431, 441, 425 that is pressed onto a port face by a retaining spring clip 432. Spring clip 432 is preferably formed with sharp edges along its outer circumference that allow it to be forced into ports 421, 422 and 424 such that its edges dig into the walls of ports 421, 422 and 424, thereby preventing spring clip 432 from coming out of port 421, 422 and 424. The center portion of spring clip 432 is preferably tapered towards a hole in the center of spring clip 432. This taper provides a means for spring clip 432 to guide a needle (not shown) that may be not be aligned with the center of sealing pad 431, 441, 425 before the needle enters sealing pad 431, 441, 425.

As shown in FIGS. 15 and 16, hollow evacuated block 430 is slidingly engaged to frame member 410 by means of studs 443 that cooperate with cylindrical wells 427. Studs 443 protrude from the side of evacuated block 430 that faces frame member 410. Cylindrical wells 427 are formed in the side of frame member 410 that faces evacuated block 430 and is opposite ports 422. Cylindrical wells 427 are formed so as to receive studs 443 of evacuated block 430 when evacuated block 430 is pressed against frame member 410.

Studs 443 carry hollow needles 426 within them and along their central axes, and shown in FIG. 16. Hollow needles 426 communicate with interior spaces 450 of evacuated block 430 by entering inner wall 428 of evacuated block 430 at point 445. Tips 457 of hollow needles 426 are covered by elastomeric seals 456 that prevent loss of vacuum from interior spaces 450.

Application of compressive force between block 430 and frame 410 urges studs 443 into wells 427. Studs 443 may travel into wells 427 until the top outer surfaces of seals 456 contact pads 425. Further travel by studs 443 will cause needle tips 457 to pierce seals 456 and to enter into pads 425. Further travel by studs 443 will cause the now unsealed hollow needle tips 457 to penetrate pads 425 entirely, thereby providing means for a fluid to travel between sample tube 423 and evacuated space 450 in block 430.

An annular space 458 is formed in the end of each stud 443 to provide a place for pierced seal 456 to reside after stud 443 has been pushed maximally into pad 425. Hollow block 430 is sealed at one end with elastomeric sealing nipple 442 retained by a spring clip (not shown) in the same manner that ports 421 and 422 are sealed by spring clips 432. Sealing nipple 442 is formed so that atmospheric pressure will cause the center portion be depressed below the level of the spring clip after block 430 has been evacuated. Loss of vacuum will enable the resiliency of the elastomer to overcome the partial pressure difference between a partly evacuated space 450 and the atmosphere, causing nipple 442 to "pop" out into an intermediate new configuration, thereby providing means for detecting loss of vacuum in block 430.

FIG. 18 is a sectional view taken through line 17—17 of FIG. 15 that illustrates a preferred embodiment of the invention in which variations in the piping diameter between port 422 and sample tube 423. The embodiment shown contains a filtration element 435 to add or remove components from a sample solution that is to be analyzed. For example, detergent removal beads may be incorporated to selectively adsorb detergents from samples derived from tissues before thermal cycling in one of the chambers so formed. It will be understood that the variations in piping diameter, which may also include the provision of additional ports or the use of one-way valves, each capable of providing different benefits, is possible and that such variations are within the scope of the of the present invention. The embodiment shown in FIG. 18 therefore in no way limits the type of piping arrangements that may be used.

Before a sample is injected into sample tube 423, a syringe means (not shown) penetrates seal 431 of port 422 and evacuates sample tube 423. A sample may then be injected into sample tube 423 through port 421, followed by a volume of air sufficient to push the sample completely out of piping 419 between port 421 and its connection 433 to the piping between port 422 and sample tube 423. The sample from port 422 is then pushed completely into sample tube 423 by means of an injection of a gas or a liquid or a combination of both. A final volume of a barrier liquid is injected from port 422 calculated to fill first chamber 434, the volume of which is greater than that of second chamber 436.

After thermal cycling or another treatment has been carried out, a syringe means (not shown) may penetrate the seal of port 422 and withdraw sufficient barrier liquid from first chamber 434 to cause the entire sample in sample tube 423 to be sucked into second chamber 436 for exposure to reagents or beads 435 having reagents attached. Following incubation, the sample mixture may be returned to sample tube 423 for further thermal cycling or for other treatment by injecting back the barrier liquid. Alternatively, the evacuated block 430 may be compressed against frame 410 to cause evacuation of sample tube 423. It should be noted that the drawings are provided for illustrative purposes and are not drawn to scale. The volumes of piping chambers to be used, in practice, typically vary from 2 to 20 microliters.

Figure 19A:
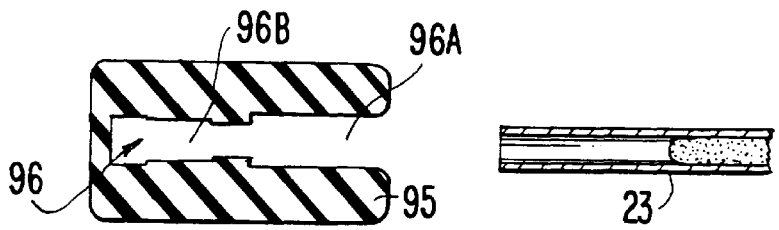
FIGS. 19A–C are partial, sectional views of a sample tube holder of the present invention.
Figure 19B:
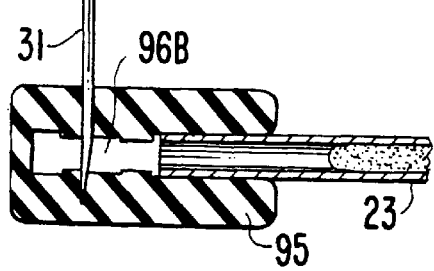
Figure 19C:
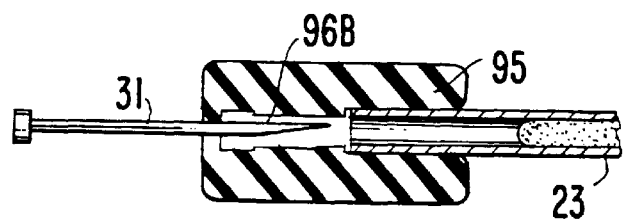

FIGS. 19A–C are sectional views of one embodiment of a tube end seal 95 and sample tube 23 containing a sample that may be used with any of the embodiments of the molecular analyzer of the present invention. Sample tube 23 may be a capillary tube. In this embodiment, inner cavity 96 of tube end seal 95 is comprised of a first portion 96A and a second portion 96B. First portion 96A of inner cavity 96 fits snugly and sealingly over the end of sample tube 23. Second portion 96B of inner cavity 96 provides a space for hollow needle 31 to enter so that substances may be injected into or removed from the sample tube 23.

FIG. 19B is a sectional view of a sample tube 23 that has been inserted into a tube end seal 95. Sample tube 23 is fitted within first portion 96A of inner cavity 96. Hollow needle 31 that has entered tube end seal 95 at right angles to the central axis of sample tube 23 is able to remove substances from or add substances to sample tube 23.

FIG. 19C is a sectional view of tube end seal 95 and sample tube 23 showing hollow needle 31 that has entered tube end seal 95 along the central axis of sample tube 23 and is able to remove substances from or add substances to sample tube 23.

Figure 20:
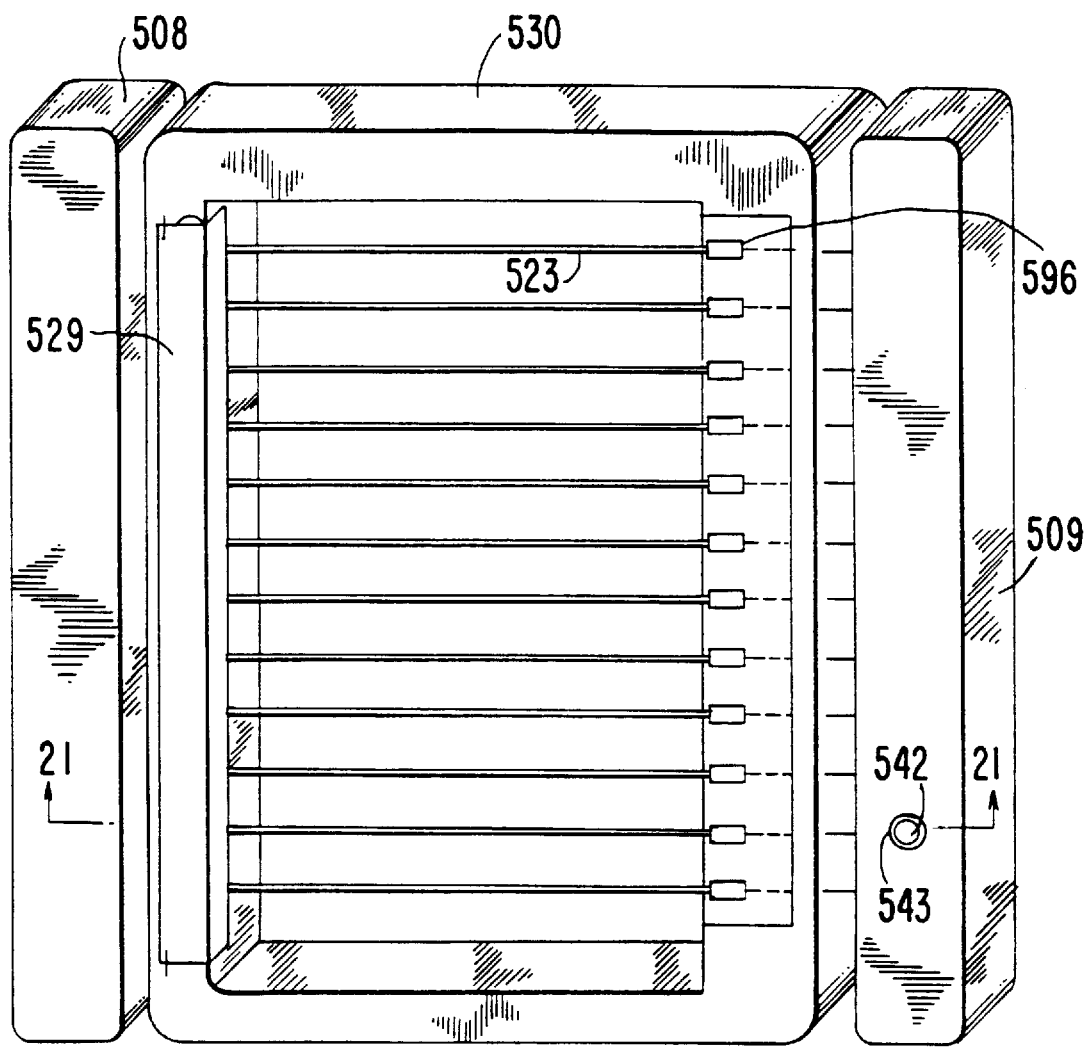
FIG. 20 is an isometric view of another preferred embodiment of a sample tube holder of the present invention.

FIG. 20 is another embodiment of a sample tube holder 500 containing 12 sample tubes 523, sealed by elastomeric end seals 581 and spanning frame 530. Frame 530 may be provided with two doors 529 which hold elastomeric end seals 581 in frame 530. FIG. 20 shows one such door 529 on the left side of frame 530. Door 529 on the right side of frame 530 is not shown in FIG. 20 so that end seals 581 may be shown. An evacuated waste chamber 508 and a reagent chamber 509 are joined to frame 530 of sample tube holder 500 on the left and right sides, respectively. Evacuated waste chamber 508 and reagent chamber 509 are slidably engageable with frame member 530 in a manner similar to that described with respect to FIG. 15.

Figure 21:
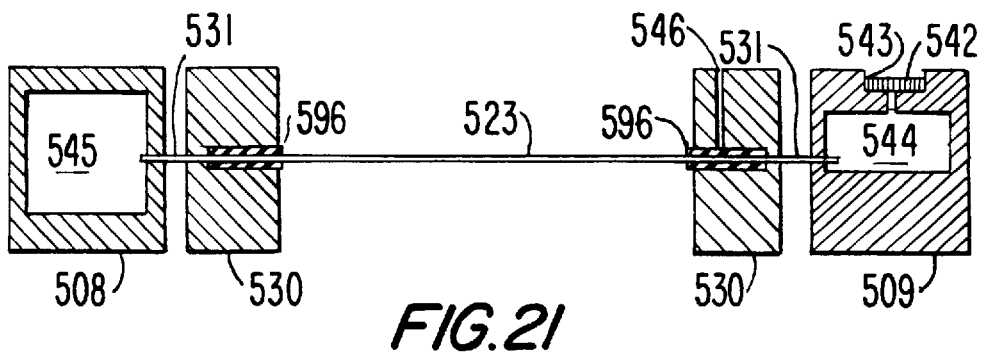
FIG. 21 is a sectional view taken along line 21—21 of FIG. 20.

FIG. 21 is a sectional view taken generally along the line 21—21 of FIG. 20 showing internal connections between evacuated waste compartment 508, needles 531, tube end seals 581, sample tube 523 and reagent chamber 509. Frame member 530 may be provided with one or more breakably sealed sample loading ports 546 formed in it that may serve as needle guides to permit introduction of substances into sample tubes 523, for example by using a syringe and needle, as illustrated in FIG. 19B. Typically, there are the same number of holes 546 provided in frame member 530 as there are sample tubes 523. Holes 546 are provided only on the side of frame member 530 that is adjacent to reagent chamber 509.

Reagent chamber 509 is provided with reagent loading ports 542, which are provided with breakable seals 543. Typically, there are the same number of reagent loading ports 542 provided in reagent chamber 509 as there are sample tubes 523. Reagent loading ports 542 provide access to space 544 and subsequently into sample tubes 523 for sequential loading of the reagents necessary to carry out the desired analysis.

Cooperative interaction between reagent chamber 509, frame member 530, and evacuated waste compartment 508 provides a fluid connection to be established and for solutions present in space 544 to have means of flowing through sample tube 523 into the evacuated waste chamber space 545, as described with reference to other embodiments of the present invention.

Figure 22A:
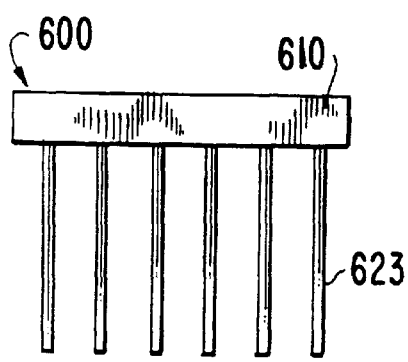
FIGS. 22A and 22C are plan views of another preferred embodiment of a sample tube holder of the present invention.
Figure 22B:
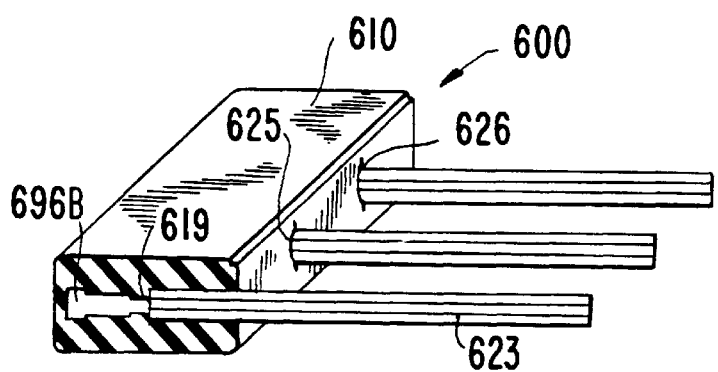
FIG. 22B is a sectional view of the sample tube holder shown in FIG. 22A.
Figure 22C:
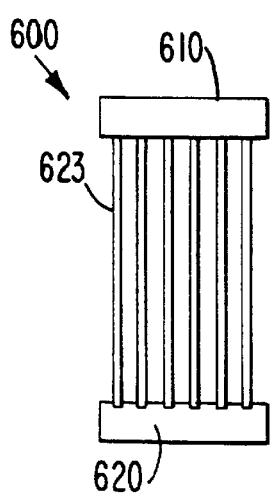

As shown in partial views in FIGS. 22A and 22B, another embodiment of sample tube holder 600 of the present invention may contain a multiplicity of sample tubes 623. Sample tube holder 600 is provided with two elastomeric members 610 and 620, which together seal both ends of one or more sample tubes 623 held between them, as shown in FIG. 22C. As shown in FIG. 22B, the inner cavities 696 that are formed in sample tube holder 600 may contain annular rings 619 that limit the degree of penetration of sample tube 623 so as to provide second portion 696B of cavity 696 behind sample tube 623, similar to cavity 96 shown in FIGS. 19A–C. Second portion 696B and cavity 696 may be useful in providing access to a sample tube 623 by means of hollow needle 31, as shown in FIGS. 19B and 19C.

Holes 625 are provided in elastomeric member 610 for receiving sample tubes 623. Slits 626 may be also be formed in elastomeric member 610 above and below holes 625 180° apart on a diameter of holes 625. Slits 626 permit communication between the outside air and the inside of a sample tube 623 held in elastomeric member 610 when such sample tube 623 has not been inserted beyond the depth reached by slit 626. In this manner a group of sample tubes 623 may be filled with a liquid test sample at the same time by capillary action.

After sample tubes 623 have been filled, second elastomeric member 620 may be placed over the ends of filled sample tubes 623, and both elastomeric members 610 and 620 may be pushed together to seal both ends of filled sample tubes 623, as shown in FIG. 22C. This configuration also permits easy access to the contents of sample tubes 623 at a later point.

Figure 23:
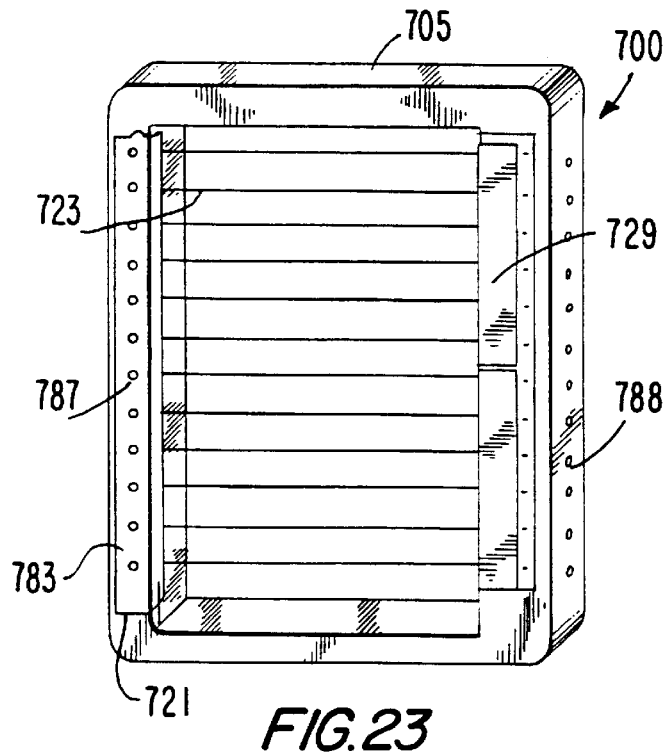
FIG. 23 is an isometric view of another preferred embodiment of a sample tube holder of the present invention.

FIG. 23 shows another embodiment of sample tube holder 700 that holds a multitude of sample tubes 723. In this embodiment, sample tubes 723 are sealed within frame member 705 of sample tube holder 705 by elastomeric tube holders 729, in a manner similar to that shown in FIGS. 6A and 6B. Frame member 705 may be provided with doors 783 to secure elastomeric tube holders 729. Doors 783 are attached to frame member 705 by hinges 721 that allow doors 783 to be opened. Door 783 that is located on the left side of frame member 705 is shown in the open position in FIG. 23. Holes 787, 788 may be formed in doors 783 or in the side of frame member 705 to guide needles (not shown) for the addition or removal of reagents or sample solutions to sample tubes 623.

Figure 26:
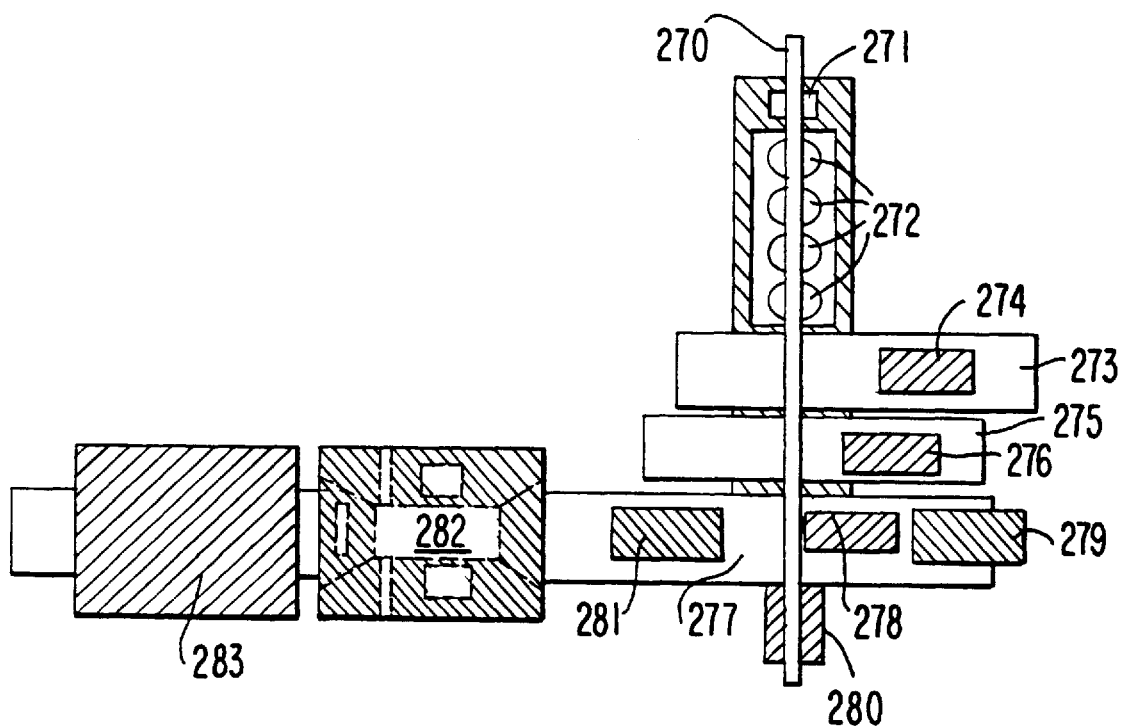
FIG. 26 is a schematic diagram of one preferred embodiment of a complete apparatus for automated PCR according to the present invention.

FIG. 26 is a schematic diagram that shows an arrangement of component devices that may cooperate together to provide one embodiment of a complete apparatus of the present invention to provide automated PCR analysis. A track mechanism 270 along which a robotic arm (not shown) may traverse provides access to a pipette tip extension tool 271 and reagent flasks 272. Tool 271 is used by the robotic arm to sealingly engage and dispose of pipette tips or disposable microsyringes (not shown). Conveyor belt 273 provides means for transporting platform 274 that may carry trays of pipette tips or disposable microsyringes (not shown) for use by the robotic arm. A second conveyor belt 275 transports platform 276 that may carry sample solutions in wells formed in a sample plate (not shown). Transport mechanism 277 provides means for moving individual groups of sample tubes 23 held in elastomeric or rigid tube holders 278 according to the present invention, moving such sample tubes 23 into position for access by the robotic arm so that sample tubes 23 may be loaded with samples.

Groups of sample tubes 23 may be held in storage 279, from which they may be dispensed to the transport mechanism 277. Alternatively, a continuous roll of sample tubes may be used, as shown in FIG. 9A. The loading of sample tubes 23 may involve cooperation with a needle means 280 attached to a syringe pump mechanism or a source of vacuum. If individual groups of sample tubes 23 are being used, after one group has been loaded, it is transported by transport mechanism 277 to rack 281. A second group of sample tubes 23 then is loaded by the robotic arm and subsequently transported to 281. When the rack is filled with groups of sample tubes 23 the transport mechanism 277 moves loaded rack 281 into thermal controller 282, which provides means for organizing sample tubes 23 into a staggered configuration as shown in FIG. 24, before thermal cycling.

When thermal cycling is complete, sample tubes 23 are transported into a detection module 283. If sample tube holders having detection reagents such as those shown in FIGS. 1, 7 or 9 are used, detection module 283 is provided with means for releasing these reagents into the sample tubes 23. If an embodiment of sample tube holders such as that shown in FIG. 15 is used, detection module 283 is provided with needle means for introducing reagents into sample tubes 23 and means for compressing the evacuated waste compartment with the sample tube holder, before transporting a group of sample tubes 23 into detection module 283, which is provided with means for detecting reaction products using, for example, any of the detection means heretofore described.

Thus is seen that a high capacity molecular analyzer and method of use that is capable of detecting specific molecules or specific parts of molecules in a sample, and which is less costly, less labor intensive and which avoid contamination of surrounding laboratory conditions, has been provided. It will be understood that the foregoing is merely illustrative of the principles of the invention, and that various modifications can be made by those skilled in the art without departing from the scope and spirit of the invention. The described embodiments are presented for the purpose of illustration rather than limitation, and the present invention is limited only by the claims which follow.

What is claimed is:

1. A molecular analyzer comprising a sample tube holder having a rigid frame with oppositely disposed sides, at least one internal chamber contained inside one of said sides of said frame, at least one sample tube, at least one internal conduit for providing communication between said at least one internal chamber and said at least one sample tube, characterized by;

said sample tube holder being further comprised of elastomeric members fitted to and held in close connection to said rigid frame;

said at least one sample tube being sealingly held between said elastomeric members;

said at least one internal chamber being filled with a detection reagent;

at least one port provided in one of said elastomeric members, said at least one port providing sealable access for a test sample to be loaded into said at least one sample tube;

an evacuated chamber contained within another of said sides of said frame and being in communication with said at least one sample tube;

means for blocking and unblocking said at least one internal conduit such that when said at least one internal conduit is blocked no communication between said at least one internal chamber and said at least one sample tube occurs, and when said at least one internal conduit is unblocked communication between said at least one internal chamber and said at least one sample tube occurs, whereby said detection reagent can flow through said at least one internal conduit, said at least one sample tube and into said evacuated chamber; and means for controlling a temperature of said test sample.

2. The molecular analyzer of claim 1 wherein said means for controlling a temperature of said test sample comprises:

a sample compartment, said sample compartment being provided with means for holding at least one said sample tube holder and a first fan for recirculating air at a first temperature within said sample compartment;

a hot air compartment, said hot air compartment being provided with a heating element and a second fan for recirculating hot air at a second temperature within said hot air compartment;

a cold air compartment, said cold air compartment being provided with a cooling element and a third fan for recirculating cold air at a third temperature within said cold air compartment;

a first door located between said sample compartment and said hot air compartment, said first door being moveable between an closed position of said first door and at least one open position of said first door;

a second door located between said sample compartment and said cold air compartment, said second door being moveable between a closed position of said second door and at least one open position of said second door; wherein:

when said first door is in said closed position of said first door and said second door is in said closed position of said second door, no air circulates between said sample compartment and said hot air compartment and no air circulates between said sample compartment and said cold air compartment;

when said first door is in said at least one open position of said first door and said second door is in said closed position of said second door, air from said sample compartment and said hot air compartment circulates between said sample compartment and said hot air compartment, and no air circulates between said sample compartment and said cold air compartment; and when said first door is in said closed position of said first door and said second door is in said at least one open position of said second door, air from said sample compartment and said cold air compartment circulates between said sample compartment and said cold air compartment, and no air circulates between said sample compartment and said hot air compartment.

3. The molecular analyzer of claim 2 wherein said sample compartment is further provided with a first section maintained at said first temperature, a second section maintained at said third temperature by said cold air recirculating between said cold air compartment and said second section of said sample compartment, and a base for holding said at least one sample tube holder comprised of a thermal conductive material dividing said sample compartment into said first and second sections; wherein: said detection reagents are maintained at said third temperature.

4. The molecular analyzer of claim 2 wherein said first temperature is a temperature optimal for DNA polymerase activity.

5. The molecular analyzer of claim 4 wherein said first temperature is lowered to a temperature optimal for DNA annealing when said second door is moved from said closed position of said second door to said at least one open position of said second door.

6. A molecular analyzer comprising a sample tube holder having a frame having two pairs of opposing sides and being provided with at least one pair of internal cavities formed within each of one of said pairs of opposing sides of said frame, and at least one sample tube having an internal volume communicating with each of said at least one pair of internal cavities, characterized by:

said at least one sample tube being sealingly held between one of said pairs of opposing sides of said frame;

at least one pair of orifices, each of said pair of orifices being provided in each of one of said pairs of opposing sides of said frame, said at least one pair of orifices providing sealable access to said at least one pair of internal cavities;

means for filling said at least one sample tube with a test sample wherein said test sample is loaded into one of said at least one pair of orifices and flows into said at least one sample tube;

means for passing at least one detection reagent through said at least one sample tube, wherein said at least one detection reagent is loaded into one of said at least one pair of orifices, flows through said at least one sample tube, and is removed from said other of said at least one pair of orifices; and means for controlling the temperature of said test sample.

7. The molecular analyzer of claim 6 wherein said means for controlling the temperature of said test sample comprises:

a sample compartment, said sample compartment being provided with means for holding at least one said sample tube holder and a first fan for recirculating air at a first temperature within said sample compartment;

a hot air compartment, said hot air compartment being provided with a heating element and a second fan for recirculating hot air at a second temperature within said hot air compartment;

a cold air compartment, said cold air compartment being provided with a cooling element and a third fan for recirculating cold air at a third temperature within said cold air compartment;

a first door located between said sample compartment and said hot air compartment, said first door being moveable between a closed position of said first door and at least one open position of said first door;

a second door located between said sample compartment and said cold air compartment, said second door being moveable between a closed position of said second door and at least one open position of said second door;

wherein:

when said first door is in said closed position of said first door and said second door is in said closed position of said second door, no air circulates between said sample compartment and said hot air compartment and no air circulates between said sample compartment and said cold air compartment;

when said first door is in said at least one open position of said first door and said second door is in said closed position of said second door, air from said sample compartment and said hot air compartment circulates between said sample compartment and said hot air compartment, and no air circulates between said sample compartment and said cold air compartment; and when said first door is in said closed position of said first door and said second door is in said at least one open position of said second door, air from said sample compartment and said cold air compartment circulates between said sample compartment and said cold air compartment, and no air circulates between said sample compartment and said hot air compartment.

8. The molecular analyzer of claim 7 wherein said sample compartment is further provided with a first section maintained at said first temperature, a second section maintained at said third temperature by said cold air recirculating between said cold air compartment and said second section of said sample compartment, and a base for holding said at least one sample tube holder comprised of a thermal conductive material dividing said sample compartment into said first and second sections; wherein: said detection reagents are maintained at said third temperature.

9. A molecular analyzer comprising a sample tube holder comprised of a rigid frame provided with oppositely disposed recesses, and at least one sample tube, characterized by:

said recesses receiving a pair of elastomeric strips;

said at least one sample tube being sealingly held between said elastomeric strips, said elastomeric strips and said at least one sample tube being together removable from said frame;

at least one internal cavity formed within one of said elastomeric strips and located behind each of said at least one sample tube holder, said at least one internal cavity communicating with an internal volume of said at least one sample tube;

at least one pair of orifices, each of said pair of orifices being provided in each of one of said pair of elastomeric strips, said at least one pair of orifices providing sealable access to said at least one internal cavity;

means for filling said at least one sample tube with a test sample wherein said test sample is loaded into one of said at least one pair of orifices and flows into said at least one sample tube;

means for passing at least one detection reagent through said at least one sample tube, wherein said at least one detection reagent is loaded into one of said at least one pair of orifices, flows through said at least one sample tube, and is removed from said other of said at least one pair of orifices; and means for controlling the temperature of said test sample.

10. The molecular analyzer of claim 9 wherein said means for controlling the temperature of said test sample comprises:

a sample compartment, said sample compartment being provided with means for holding at least one said sample tube holder and a first fan for recirculating air at a first temperature within said sample compartment;

a hot air compartment, said hot air compartment being provided with a heating element and a second fan for recirculating hot air at a second temperature within said hot air compartment;

a cold air compartment, said cold air compartment being provided with a cooling element and a third fan for recirculating cold air at a third temperature within said cold air compartment;

a first door located between said sample compartment and said hot air compartment, said first door being moveable between a closed position of said first door and at least one open position of said first door;

a second door located between said sample compartment and said cold air compartment, said second door being moveable between a closed position of said second door and at least one open position of said second door; wherein:

when said first door is in said closed position of said first door and said second door is in said closed position of said second door, no air circulates between said sample compartment and said hot air compartment and no air circulates between said sample compartment and said cold air compartment;

when said first door is in said at least one open position of said first door and said second door is in said closed position of said second door, air from said sample compartment and said hot air compartment circulates between said sample compartment and said hot air compartment, and no air circulates between said sample compartment and said cold air compartment; and when said first door is in said closed position of said first door and said second door is in said at least one open position of said second door, air from said sample compartment and said cold air compartment circulates between said sample compartment and said cold air compartment, and no air circulates between said sample compartment and said hot air compartment.

11. The molecular analyzer of claim 10 wherein said sample compartment is further provided with a first section maintained at said first temperature, a second section maintained at said third temperature by said cold air recirculating between said cold air compartment and said second section of said sample compartment, and a base for holding said at least one sample tube holder comprised of a thermal conductive material dividing said sample compartment into said first and second sections; wherein: said detection reagents are maintained at said third temperature.

12. A molecular analyzer comprising a sample tube holder comprised of a rigid frame, and at least one sample tube, characterized by:

said sample tube holder being further provided with a pair of oppositely disposed elastomeric strips;

said at least one sample tube being sealingly held between said elastomeric strips;

at least one internal chamber filled with a detection reagent, said at least one internal chamber being contained inside one of said elastomeric strips;

at least one port provided in one of said elastomeric strips, said at least one port providing sealable access for a test sample to be loaded into said at least one sample tube;

an evacuated chamber located within another of said elastomeric strips;

means for providing a pathway between said at least one internal chamber and said evacuated chamber whereby said detection reagent flows from said internal chamber through said at least one sample tube and into said evacuated chamber; and means for controlling the temperature of said test sample.

13. The molecular analyzer of claim 12 wherein said means for controlling the temperature of said test sample comprises:

a sample compartment, said sample compartment being provided with means for holding at least one said sample tube holder and a first fan for recirculating air within said sample compartment;

a hot air compartment, said hot air compartment being provided with a heating element and a second fan for recirculating hot air within said hot air compartment;

a cold air compartment, said cold air compartment being provided with a cooling element and a third fan for recirculating cold air within said cold air compartment;

a first door located between said sample compartment and said hot air compartment, said first door being moveable between a closed position of said first door and at least one open position of said first door;

a second door located between said sample compartment and said cold air compartment, said second door being moveable between a closed position of said second door and at least one open position of said second door; wherein:

when said first door is in said closed position of said first door and said second door is in said closed position of said second door, no air circulates between said sample compartment and said hot air compartment and no air circulates between said sample compartment and said cold air compartment;

when said first door is in said at least one open position of said first door and said second door is in said closed position of said second door, air from said sample compartment and said hot air compartment circulates between said sample compartment and said hot air compartment, and no air circulates between said sample compartment and said cold air compartment; and when said first door is in said closed position of said first door and said second door is in said at least one open position of said second door, air from said sample compartment and said cold air compartment circulates between said sample compartment and said cold air compartment, and no air circulates between said sample compartment and said hot air compartment.

14. The molecular analyzer of claim 13 wherein said sample compartment is further provided with a first section, a second section maintained at the same temperature as said cold air compartment by said cold air recirculating between said cold air compartment and said second section of said sample compartment, and said means for holding said at least one sample tube holder is comprised of a thermal conductive base dividing said sample compartment into said first and second sections; whereby; said detection reagents are maintained at the said third temperature.

15. A molecular analyzer having a plurality of sample tubes, characterized by:
a pair of oppositely disposed elastomeric members;
said plurality of sample tubes being sealingly held between said elastomeric members;
at least one internal chamber, said at least one internal chamber being filled with a detection reagent and contained inside one of said elastomeric members;
at least one internal conduit for providing communication between said at least one internal chamber and said at least one sample tube;
at least one internal cavity formed behind each of said at least one sample tube, said at least one internal cavity communicating with an internal volume of said at least one sample tube;
at least one port provided in one of said elastomeric members, said at least one port providing sealable access for a test sample to be loaded into said at least one internal cavity;
an evacuated chamber located within another of said elastomeric members and being in communication with said at least one sample tube;
means for blocking and unblocking said at least one internal conduit such that when said at least one internal conduit is blocked no communication between said at least one internal chamber and said at least one sample tube occurs, and when said at least one internal conduit is unblocked communication between said at least one internal chamber and said at least one sample tube occurs; and
means for controlling the temperature of said test sample.

16. The molecular analyzer of claim 15 wherein said means for controlling the temperature of said test sample comprises:
a sample compartment, said sample compartment being provided with means for holding at least one said sample tube holder and a first fan for recirculating air within said sample compartment;
a hot air compartment, said hot air compartment being provided with a heating element and a second fan for recirculating hot air within said hot air compartment;
a cold air compartment, said cold air compartment being provided with a cooling element and a third fan for recirculating cold air within said cold air compartment;
a first door located between said sample compartment and said hot air compartment, said first door being moveable between a closed position of said first door and at least one open position of said first door;
a second door located between said sample compartment and said cold air compartment, said second door being moveable between a closed position of said second door and at least one open position of said second door; wherein:
when said first door is in said closed position of said first door and said second door is in said closed position of said second door, no air circulates between said sample compartment and said hot air compartment and no air circulates between said sample compartment and said cold air compartment;
when said first door is in said at least one open position of said first door and said second door is in said closed position of said second door, air from said sample compartment and said hot air compartment circulates between said sample compartment and said hot air compartment, and no air circulates between said sample compartment and said cold air compartment; and
when said first door is in said closed position of said first door and said second door is in said at least one open position of said second door, air from said sample compartment and said cold air compartment circulates between said sample compartment and said cold air compartment, and no air circulates between said sample compartment and said hot air compartment.

17. The molecular analyzer of claim 16 wherein said sample compartment is further provided with a first section, a second section maintained at the same temperature as said cold air compartment by said cold air recirculating between said cold air compartment and said second section of said sample compartment, and said means for holding said at least one sample tube holder is comprised of a thermal conductive base dividing said sample compartment into said first and second sections; whereby; said detection reagents are maintained at said third temperature.

18. A thermal controller for a molecular analyzer comprising:
a sample compartment, said sample compartment being provided with means for holding at least one sample tube holder and a first fan for recirculating air at a first temperature within said sample compartment;
a hot air compartment, said hot air compartment being provided with a heating element and a second fan for recirculating hot air at a second temperature within said hot air compartment;
a cold air compartment, said cold air compartment being provided with a cooling element and a third fan for recirculating cold air at a third temperature within said cold air compartment;
a first door located between said sample compartment and said hot air compartment, said first door being moveable between a closed position of said first door and at least one open position of said first door;
a second door located between said sample compartment and said cold air compartment, said second door being moveable between a closed position of said second door and at least one open position of said second door; wherein:
when said first door is in said closed position of said first door and said second door is in said closed position of said second door, no air circulates between said sample compartment and said hot air compartment and no air circulates between said sample compartment and said cold air compartment;
when said first door is in said at least one open position of said first door and said second door is in said closed position of said second door, air from said sample compartment and said hot air compartment circulates between said sample compartment and said hot air compartment, and no air circulates between said sample compartment and said cold air compartment; and when said first door is in said closed position of said first door and said second door is in said at least one open position of said second door, air from said sample compartment and said cold air compartment circulates between said sample compartment and said cold air compartment, and no air circulates between said sample compartment and said hot air compartment.

19. The thermal controller of claim 18 wherein said first temperature is a temperature optimal for DNA polymerase activity.

20. The thermal controller of claim 19 wherein said second temperature is maintained at 200° Celsius, and said third temperature is maintained at 0° Celsius.

21. The thermal controller of claim 20 wherein said first temperature is raised to approximately 96° Celsius when said first door is moved from said closed position of said first door to said at least one open position of said first door.

22. The thermal controller of claim 19 wherein said first temperature is lowered to a temperature optimal for DNA annealing when said second door is moved from said closed position of said second door to said at least one open position of said second door.

23. The thermal controller of claim 18 wherein said sample compartment is further provided with a first section, a second section maintained at said third temperature by said cold air recirculating between said cold air compartment and said second section of said sample compartment, and said means for holding said at least one sample tube holder is comprised of a thermal conductive base dividing said sample compartment into said first and second sections; whereby; at least one detection reagent contained within said sample tube holder is maintained at said third temperature.

24. A molecular analyzer comprising a sample tube holder comprised of a rigid frame having two pairs of opposing sides, at least one sample tube held between one pair of opposing sides, one side being provided with at least one well formed in said side and at least one internal cavity formed within the other side of said pair of opposing sides of said frame and located behind and communicating with an internal volume of said at least one sample tube, characterized by:

said at least one sample tube being sealingly held between one of said pairs of opposing sides of said frame;

at least one sample port provided within said side of said other of said one of said pairs of opposing sides of said frame, said at least one sample port providing sealable access for a test sample to be loaded into said at least one sample tube;

at least one reagent port provided within said side of said other of said one of said pairs of opposing sides of said frame, said at least one reagent port providing sealable access for at least one detection reagent to be loaded into said at least one sample tube;

an evacuated block provided with an interior hollow chamber and at least one stud for engaging said at least one well such that when said at least one stud is received by said at least one well, a fluid path is provided between said at least one internal cavity and said interior hollow chamber; and means for controlling the temperature of said test sample.

25. The molecular analyzer of claim 24 wherein said means for controlling the temperature of said test sample comprises:

a sample compartment, said sample compartment being provided with means for holding at least one said sample tube holder and a first fan for recirculating air within said sample compartment;

a hot air compartment, said hot air compartment being provided with a heating element and a second fan for recirculating hot air within said hot air compartment;

a cold air compartment, said cold air compartment being provided with a cooling element and a third fan for recirculating cold air within said cold air compartment;

a first door located between said sample compartment and said hot air compartment, said first door being moveable between a closed position of said first door and at least one open position of said first door;

a second door located between said sample compartment and said cold air compartment, said second door being moveable between a closed position of said second door and at least one open position of said second door;

wherein:

when said first door is in said closed position of said first door and said second door is in said closed position of said second door, no air circulates between said sample compartment and said hot air compartment and no air circulates between said sample compartment and said cold air compartment;

when said first door is in said at least one open position of said first door and said second door is in said closed position of said second door, air from said sample compartment and said hot air compartment circulates between said sample compartment and said hot air compartment, and no air circulates between said sample compartment and said cold air compartment; and when said first door is in said closed position of said first door and said second door is in said at least one open position of said second door, air from said sample compartment and said cold air compartment circulates between said sample compartment and said cold air compartment, and no air circulates between said sample compartment and said hot air compartment.

26. The molecular analyzer of claim 25 wherein said sample compartment is further provided with a first section, a second section maintained at the same temperature as said cold air compartment by said cold air recirculating between said cold air compartment and said second section of said sample compartment, and said means for holding said at least one sample tube holder is comprised of a thermal conductive base dividing said sample compartment into said first and second sections; whereby; said detection reagents are maintained at said third temperature.

27. A molecular analyzer comprising a sample tube holder comprised of a rigid frame having two pairs of opposing sides, and at least one sample tube sealingly held between one pair of said opposing sides, characterized by:

a reagent chamber having an internal volume and slidably engageable with a side of one of said pairs of opposing sides, said reagent chamber being provided with at least one reagent port providing sealable access for at least one reagent to be loaded into said reagent chamber;

an evacuated chamber having an internal volume and slidably engageable with another side of one of said pairs of opposing sides, whereby a fluid passageway is provided between said internal volume of said reagent chamber, said at least one sample tube and said internal volume of said evacuated chamber when said reagent chamber and said evacuated chamber are engaged with said frame; and means for controlling the temperature of a test sample disposed within said at least one sample tube.

28. The molecular analyzer of claim 27 wherein said means for controlling the temperature of said test sample comprises:

a sample compartment, said sample compartment being provided with means for holding at least one said sample tube holder and a first fan for recirculating air within said sample compartment;

a hot air compartment, said hot air compartment being provided with a heating element and a second fan for recirculating hot air within said hot air compartment;

a cold air compartment, said cold air compartment being provided with a cooling element and a third fan for recirculating cold air within said cold air compartment;

a first door located between said sample compartment and said hot air compartment, said first door being moveable between a closed position of said first door and at least one open position of said first door;

a second door located between said sample compartment and said cold air compartment, said second door being moveable between a closed position of said second door and at least one open position of said second door; wherein:

when said first door is in said closed position of said first door and said second door is in said closed position of said second door, no air circulates between said sample compartment and said hot air compartment and no air circulates between said sample compartment and said cold air compartment;

when said first door is in said at least one open position of said first door and said second door is in said closed position of said second door, air from said sample compartment and said hot air compartment circulates between said sample compartment and said hot air compartment, and no air circulates between said sample compartment and said cold air compartment; and when said first door is in said closed position of said first door and said second door is in said at least one open position of said second door, air from said sample compartment and said cold air compartment circulates between said sample compartment and said cold air compartment, and no air circulates between said sample compartment and said hot air compartment.

29. The molecular analyzer of claim 28 wherein said sample compartment is further provided with a first section, a second section maintained at the same temperature as said cold air compartment by said cold air recirculating between said cold air compartment and said second section of said sample compartment, and said means for holding said at least one sample tube holder is comprised of a thermal conductive base dividing said sample compartment into said first and second sections; whereby; said detection reagents are maintained at said third temperature.

* * * * *